United States Patent
Adachi et al.

(10) Patent No.: US 8,914,100 B2
(45) Date of Patent: *Dec. 16, 2014

(54) ELECTROENCEPHALOGRAM MEASUREMENT SYSTEM, ELECTROENCEPHALOGRAM MEASUREMENT METHOD, AND PROGRAM THEREOF

(75) Inventors: Shinobu Adachi, Nara (JP); Jun Ozawa, Nara (JP); Yoshihisa Terada, Tokyo (JP); Koji Morikawa, Kyoto (JP)

(73) Assignee: Panasonic Corporation, Osaka (JP)

( * ) Notice: Subject to any disclaimer, the term of this patent is extended or adjusted under 35 U.S.C. 154(b) by 229 days.

This patent is subject to a terminal disclaimer.

(21) Appl. No.: 13/435,314

(22) Filed: Mar. 30, 2012

(65) Prior Publication Data

US 2012/0191000 A1 Jul. 26, 2012

Related U.S. Application Data

(63) Continuation of application No. PCT/JP2011/003333, filed on Jun. 13, 2011.

(30) Foreign Application Priority Data

Jun. 14, 2010 (JP) ................................ 2010-134766

(51) Int. Cl.
*A61B 5/04* (2006.01)
*A61B 5/048* (2006.01)

(52) U.S. Cl.
CPC ......... *A61B 5/048* (2013.01); *A61B 2560/0276* (2013.01)
USPC ...................................................... 600/544

(58) Field of Classification Search
CPC .. A61B 5/0476; A61B 5/04012; A61B 5/048; A61B 5/0478; A61B 5/0482

USPC .................................................. 600/544, 545
See application file for complete search history.

(56) References Cited

U.S. PATENT DOCUMENTS 8,473,045 B2 * 6/2013 Terada et al. ................. 600/545
2009/0259137 A1 * 10/2009 Delic et al. .................... 600/545

(Continued)

FOREIGN PATENT DOCUMENTS

JP 06-154181 A 6/1994
JP 07-003347 U 1/1995

(Continued)

OTHER PUBLICATIONS

International Search Report for corresponding International Application No. PCT/JP2011/003333 mailed Jul. 26, 2011.

(Continued)

*Primary Examiner* — Etsub Berhanu
(74) *Attorney, Agent, or Firm* — Renner, Otto, Boisselle & Sklar, LLP

(57) ABSTRACT

An exemplary electroencephalogram measurement system includes: a frequency analysis section for, analyzing a frequency power of the electroencephalogram signal of a user with respect to each set of a reference electrode and a measurement electrode; an insufficient electrode determination section for, through comparison of the analyzed frequency power against a first threshold value, distinguishing whether a state of attachment of each electrode is sufficient or not; and an insufficiency cause estimation section for determining the number of insufficient electrodes distinguished as insufficiently worn, determining a position at which each insufficient electrode is in contact with the user, and estimating a cause for the insufficient state of attachment of the insufficient electrode or electrodes that corresponds to the determined number of insufficient electrodes and position of each insufficient electrode by referring to insufficiency pattern data.

17 Claims, 24 Drawing Sheets

(56) References Cited

U.S. PATENT DOCUMENTS

| | | |
|---|---|---|
| 2009/0270753 A1 | 10/2009 | Adachi et al. |
| 2010/0191140 A1 | 7/2010 | Terada et al. |
| 2012/0029336 A1 | 2/2012 | Terada et al. |

FOREIGN PATENT DOCUMENTS

| | | |
|---|---|---|
| JP | 2006-006665 A | 1/2006 |
| JP | 2006-014833 A | 1/2006 |
| JP | 2006-212348 A | 8/2006 |
| JP | 4465414 B | 2/2010 |
| WO | 2010/004698 A1 | 1/2010 |
| WO | 2011/074186 A1 | 6/2011 |

OTHER PUBLICATIONS

Donchin et al., "The Mental Prosthesis: Assessing the Speed of a P300-Based Brain-Computer Interface", Transactions on Rehabilitation Engineering 2000, vol. 8, Jun. 2000 (cited in [0006] of the specification).

* cited by examiner

FIG. 4

| | NORMAL | SHIFTING MEASUREMENT ELECTRODE 1 | SHIFTING MEASUREMENT ELECTRODE 2 | SHIFTING REFERENCE ELECTRODE | DISENGAGING GROUND |
|---|---|---|---|---|---|
| Ch1 AMOUNT OF MIXED AC NOISE | 82.3 | 80.3 | 81.4 | 42.9 | 35502.3 |
| Ch2 AMOUNT OF MIXED AC NOISE | 121.8 | 123.1 | 124.8 | 56.1 | 151739.9 |
| Ch1 TOTAL FREQUENCY POWER | 5.2 | 93.7 | 4.6 | 357.6 | 594.1 |
| Ch2 TOTAL FREQUENCY POWER | 2.8 | 3.4 | 67.1 | 194.6 | 2430.6 |

[UNIT: μV^2]

FIG.8

| | RESULT OF INSUFFICIENT ELECTRODE DETERMINATION | INSUFFICIENCY CAUSE ESTIMATION | REMEDY (OUTPUT) |
|---|---|---|---|
| (a) | NO INSUFFICIENT ELECTRODES | — | NOTIFICATION OF PROPERNESS |
| (b) | PLURALITY OF INSUFFICIENT ELECTRODES IN PROXIMITY | DISAGREEMENT BETWEEN HEAD SHAPE AND HOUSING SHAPE, DISAGREEMENT OCCURRING NEAR INSUFFICIENT ELECTRODES | INSTRUCTION TO EXCHANGE HEADSET |
| (c) | CERTAIN SPATIAL PATTERN OF INSUFFICIENT ELECTRODES | DISAGREEMENT BETWEEN HEAD SHAPE AND HOUSING SHAPE | INSTRUCTION TO EXCHANGE HEADSET |
| (d) | SINGLE INSUFFICIENT ELECTRODE AT HAIRED SITE | HAIR PINCHING | INSTRUCTION TO AVOID HAIR AT INSUFFICIENT ELECTRODE |

*FIG.18*

| ELECTRODE POSITION | | | INSUFFICIENCY PATTERN | | | |
|---|---|---|---|---|---|---|
| x | y | z | DENT IN CENTRAL PORTION | LONGER VERTICALLY THAN LATERALLY | REFERENCE ELECTRODE DISENGAGEMENT | ... |
| 0.00 | −1.00 | −0.03 |  | × | × | ... |
| 0.00 | −0.72 | 0.70 |  | × | × | ... |
| 0.00 | −0.39 | 0.92 | × |  | × | ... |
| 0.00 | 0.00 | 1.00 | × |  | × | ... |
| 0.00 | 0.39 | 0.92 | × |  | × | ... |
| 0.00 | 0.72 | 0.70 |  | × | × | ... |
| 0.00 | 1.00 | −0.03 |  | × | × | ... |

|  | SIZE | SHAPE 1 | SHAPE 2 |
|---|---|---|---|
| HOUSING A | S | LONGER LATERALLY THAN VERTICALLY | NORMAL |
| HOUSING B | S | LONGER LATERALLY THAN VERTICALLY | DENT IN THE CENTRAL PORTION |
| HOUSING C | S | LONGER VERTICALLY THAN LATERALLY | NORMAL |
| HOUSING D | S | LONGER VERTICALLY THAN LATERALLY | DENT IN THE CENTRAL PORTION |
| HOUSING E | M | LONGER LATERALLY THAN VERTICALLY | NORMAL |
| ... | ... | ... | ... |

ELECTROENCEPHALOGRAM MEASUREMENT SYSTEM, ELECTROENCEPHALOGRAM MEASUREMENT METHOD, AND PROGRAM THEREOF

This is a continuation of International Application No. PCT/JP2011/003333, with an international filing date of Jun. 13, 2011, which claims priority of Japanese Patent Application No. 2010-134766, filed on Jun. 14, 2010, the contents of which are hereby incorporated by reference.

BACKGROUND

1. Technical Field

The present disclosure relates to a system for measuring an electroencephalogram of a user who wears on his or her head a housing having electrodes provided thereon. Specifically, the present disclosure relates to an electroencephalogram measurement system for determining states of attachment of electrodes, and estimating an insufficiency cause in accordance with the position of any insufficient electrode.

2. Description of the Related Art

Conventionally, as a method of measuring an electroencephalogram (Electroencephalogram: EEG), a method which records changes in the potentials of two points on the scalp (potentials of a reference electrode and an electrode for measurement) is known. An electroencephalogram is an electrical signal which is measured as a potential difference between the reference electrode and the electrode for measurement. An electroencephalogram is supposed to reflect encephalic activities (electrical activities of the cranial nerve cells), and more specifically, electrical activities of the cerebral cortex. As compared to other methods of measuring encephalic activities in noninvasive manners, the aforementioned method of measuring potential changes as an electroencephalogram has the advantages of high time resolution and easy measurement. At medical institutions, electroencephalogram measurement methods based on electrical potentials have conventionally been used for diagnosis of epilepsy, Alzheimer's disease, and the like. At research institutions, electroencephalogram measurement methods have been utilized as tools for basis research on the process of perception and cognizance, which is information processing in the human brain.

In order to measure an electroencephalogram, it is necessary to attach electrodes on the head. Therefore, a method of electrode attachment will be described. First, paste is applied on an electrode. The paste is a cream having a high electrical conductivity, serving to enhance the electrical conductivity between the skin and the electrode. A specialist (a third person) other than the user ensures that the electrode having the paste applied thereon is in tight contact with the scalp of the user. Conventionally, since the electrode and an electroencephalograph would be connected via a lead wire which permits high freedom, the third person would be able to attach the electrode at any arbitrary position on the head of the user. Moreover, in the case of taking multi-point measurements by utilizing a plurality of electrodes, there exists a method which employs an electrode cap having high contraction and expansion properties. Both methods allow the electrodes to be stably attached at predetermined positions on the head, without being affected by the head shape of the user. For the electrode attachment, about several minutes is required for each electrode, which is a relatively long time. However, the time required for electrode attachment has never been regarded as a problem because, in the past, this has all been in a preparatory procedure for diagnosis or basis research.

In recent years, the downsizing of electroencephalographs and increased accuracy of signal processing techniques are making it possible to develop electroencephalogram interfaces for inferring the psychological state of a user based on an electroencephalogram and inferring his or her intent of manipulation as to how they want to manipulate a device, or intent of selection as to which one of a plurality of options they want to select.

For example, as an electroencephalogram interface for use with a healthy user, Emanuel Donchin and two others, "The Mental Prosthesis: Assessing the Speed of a P300-Based Brain-Computer Interface", TRANSACTIONS ON REHABILITATION ENGINEERING 2000, Vol. 8, June 2000 discloses an electroencephalogram interface which infers an intent of selection of a user. Among event-related potentials of the electroencephalogram, the electroencephalogram interface of Donchin et al. uses a characteristic signal component called "P300" to distinguish an option that a user wishes to select. As used herein, an "event-related potential" refers to a transient potential fluctuation in the brain, which is a portion of the electroencephalogram and which occurs in temporal relationship with an external or internal event. Moreover, "P300" refers to an event-related potential component, in an electroencephalogram signal at 20 milliseconds to 400 milliseconds as reckoned from a given event, having a positive (plus direction) amplitude peak.

However, in such manners of use, which require lead wires or a special cap to be attached with the help of a specialist, it is difficult for a user in a daily-life environment to wear the electrodes by himself or herself, have their electroencephalogram measured, and have the resultant electroencephalogram used for an electroencephalogram interface or the like. Now, an example will be discussed where an electroencephalogram measurement apparatus (electrodes and an amplifier) is incorporated in a wearable device such as a head-mount display (Head-Mount-Display: HMD) or a headset as a housing for electroencephalogram measurement to measure an electroencephalogram. A housing such as an HMD or a headset, for example, has a high rigidity as compared to the aforementioned lead wires or electrode cap, and is easy to wear. Therefore, it is not difficult for the user himself or herself to, as soon as wearing the HMD or headset, position any electrode for electroencephalogram measurement that is incorporated in the housing so as to be in the neighborhood where measurement is expected to be taken.

In the aforementioned conventional technique, the user himself or herself needs to apply paste on the electrodes. Furthermore, after the device is detached, the paste remaining on the electrodes and in the places where the electrodes have been disposed must be wiped off by the user himself or herself. Therefore, in order for the user to easily wear an electroencephalogram measurement device by himself or herself, it is an example to adopt electrodes which do not require use of paste (hereinafter referred to as "dry electrodes").

However, use of dry electrodes presents a problem in wearing stability. As one example, when a force acts on a dry electrode, the state of contact between the skin and the dry electrode will change because there is no paste. This results in the electrode position changing even though contact with the skin may be maintained ("electrode shifting"), or the electrode becoming lifted off the skin to create a space between the skin and the electrode, thus disabling electroencephalogram measurement ("electrode disengagement").

Note that a paste has a high viscosity, and serves not only to enhance the electrical conductivity between the skin and the electrode, but also to prevent electrode shifting and electrode disengagement. This conserves the state of contact between the skin and the electrode even when the position of an electrode is slightly changed due to a force acting thereupon, because the paste with a high viscosity will then be deformed to allow the electroencephalogram to be properly measured.

When electrode shifting occurs, the skin will be rubbing against the electrode surface, so that noises may likely be mixed in the measured electroencephalogram. If an electrode disengagement occurs, electroencephalogram measurement will be so affected that it is made impossible. Since the user will not always be in a resting state but will undergo various motions in a daily-life environment, insufficiencies concerning electrode contact, such as electrode shifting and electrode disengagement, are likely to occur. In the present specification, an electrode which has become insufficient in terms of contact or attachment will be referred to as an "insufficient electrode". An insufficient electrode is an electrode in a poor state of attachment, i.e., an electrode which is not in a good state of attachment with the skin, such that an electroencephalogram cannot be properly measured.

In order to reduce insufficiencies of measurement due to such electrode shifting and electrode disengagement, it is necessary to quickly detect if a situation obstructing electroencephalogram measurement has occurred. Conventionally known methods for detecting an unfavorable situation for electroencephalogram measurement are: the methods in Japanese Examined Utility Model Publication No. 7-3347 ("hereinafter Patent Document 1"); Japanese Laid-Open Patent Publication No. 2006-212348 ("hereinafter Patent Document 2"); Japanese Laid-Open Patent Publication No. 2006-6665 ("hereinafter Patent Document 3"); and the specification of Japanese Patent No. 4465414 ("hereinafter Patent Document 4"), which will be described below.

Patent Document 1 discloses a method of flowing a weak current through an electroencephalogram electrode, calculating a resistance value (contact resistance) between the skin and the electrode from the measured voltage value, and estimating a state of contact between the skin and the electrode. As a result, insufficiencies concerning the state of electrode attachment are detected (see Patent Document 1, page 3, left column, second paragraph).

In Patent Document 2, a coil is provided near an electrode (FIG. 2 of Patent Document 2), and a voltage is applied to the coil. Based on whether a resultant induced current in the electrode is superposed on the electroencephalogram waveform or not, it is determined as to whether the electrode and the scalp are in contact (Patent paragraph [0038] of Document 2).

In Patent Document 3, measurements are taken of a plurality of "electroencephalogram channels", each electroencephalogram channel defining an electroencephalogram signal to be measured based on the potential difference between a pair of electrodes. In other words, a plurality of pairs of electrodes are provided, and an electroencephalogram signal is measured by each pair. Then, for each electroencephalogram channel, a Signal (=signal to be measured) and Noise (=any signal other than the signal to be measured) are calculated. Through a comparison of the S/N ratio against a threshold value, it is determined as to which electroencephalogram channel is suffering from a measurement insufficiency (paragraph [0028] of Patent Document 3).

In Patent Document 4, insufficiencies of wearing between electrodes for electroencephalogram measurement is distinguished via impedance checks. This makes it possible to identify whether electrodes are in contact with the skin of the user or not. The impedance check, as used in Patent Document 4, is an approach of flowing a very minute amount of current between two electrodes to measure a value of resistance existing between the places where the two electrodes are in contact with the skin. When electrode disengagement, user perspiration, or the like occurs to prevent proper detection of an electroencephalogram, there is an increase in the resistance value between the electrodes. Therefore, by performing impedance checks to measure resistance values between electrodes, it becomes possible to determine which combination of electrodes fails to attain proper contact (paragraphs [0167], [0168] of Patent Document 4).

SUMMARY

One non-limiting, and exemplary embodiment provides a technique to, in an electroencephalogram measurement to be taken in a daily-life environment, determine which one of a plurality of electrodes has been made insufficient by what kind of cause, estimate causes of insufficiency, and easily realize stable electroencephalogram measurements.

In one general aspect, an electroencephalogram measurement system disclosed herein comprises: an electroencephalogram measurement section having a plurality of electrodes being disposed in one housing, the plurality of electrodes including a reference electrode, measurement electrodes and a ground, for measuring an electroencephalogram signal between the reference electrode and a measurement electrode on the basis of the ground, the plurality of electrodes constituting a plurality of electroencephalogram measurement channels, such that each electroencephalogram measurement channel is defined by at least the reference electrode and a measurement electrode; an electrode position storing section for storing positions at which the plurality of electrodes respectively come in contact with a user when the user wears the electroencephalogram measurement section; a frequency analysis section for analyzing a frequency power of the electroencephalogram signal measured by the electroencephalogram measurement section with respect to each electroencephalogram measurement channel; an insufficient electrode determination section for distinguishing whether a state of attachment of each electrode is sufficient or not by comparing the frequency power analyzed by the frequency analysis section against a predetermined first threshold value; and an insufficiency cause estimation section for: determining the number of insufficient electrodes distinguished as insufficiently worn at the insufficient electrode determination section; determining a position at which each insufficient electrode determined as insufficiently worn at the insufficient electrode determination section is in contact with the user, by referring to the positions of the plurality of electrodes stored in the electrode position storing section; and estimating a cause for the insufficient state of attachment of the insufficient electrode or electrodes that corresponds to the determined number of insufficient electrodes and position of each insufficient electrode, by referring to insufficiency pattern data defining associations between the number of insufficient electrodes, the position at which each insufficient electrode comes in contact with the user, and causes for the insufficient state of attachment of the insufficient electrode or electrodes.

These general and specific aspects may be implemented using a system, a method, and a computer program, and any combination of systems, methods, and computer programs.

Additional benefits and advantages of the disclosed embodiments will be apparent from the specification and Figures. The benefits and/or advantages may be individually provided by the various embodiments and features of the specification and drawings disclosure, and need not all be provided in order to obtain one or more of the same.

Figure 2:
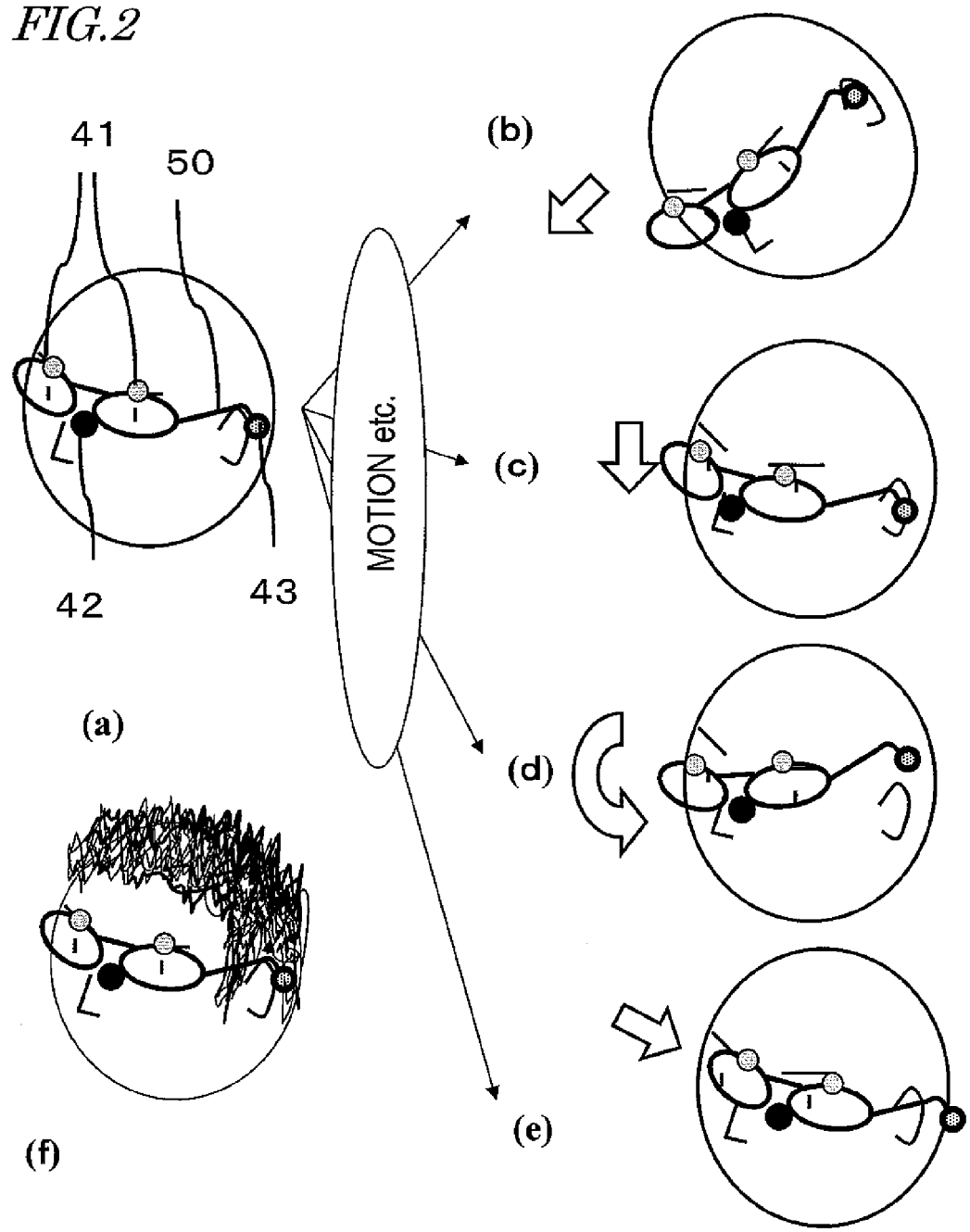

Portions (a) to (f) of FIG. 2 are diagrams showing an eyeglass-type head-mount display (HMD) 50 in which dry electrodes for electroencephalogram measurement are incorporated, and their state of attachment.

Figure 3A:
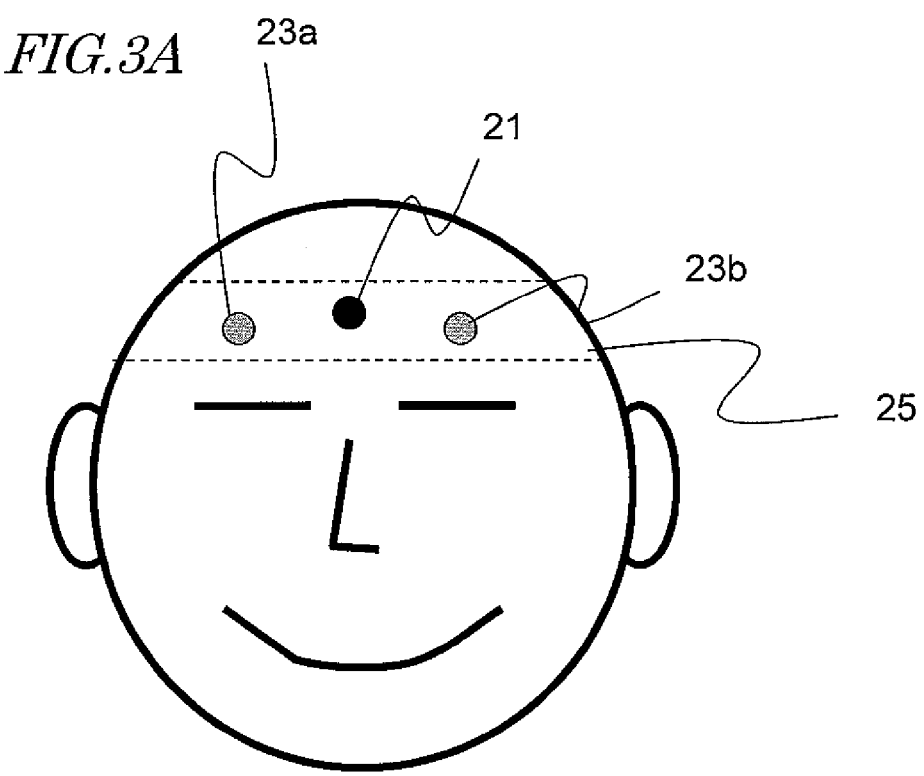
Figure 3B:
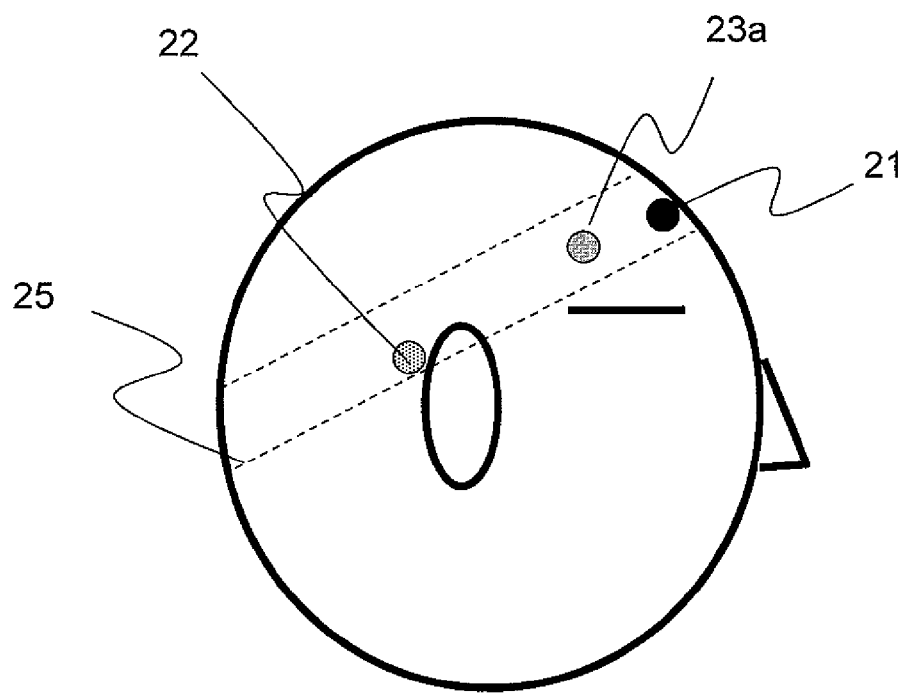

FIGS. 3A and 3B are diagrams showing positioning of electrodes which are provided within the range of the shape of a hair band 25 of an HMD.

FIG. 4 is a diagram showing results of an electroencephalogram analysis.

Figure 5:
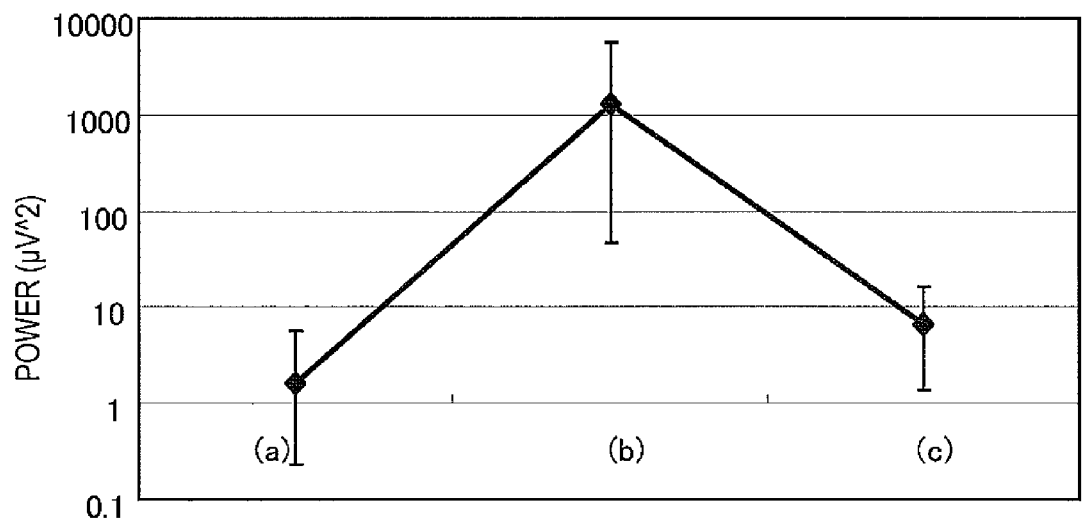

FIG. 5 is a diagram showing an average value of amounts of mixed AC noise of all test subjects and an extent of variations among all test subjects, in the three states of: (a) normal state; (b) disengaging the ground; and (c) disengaging a measurement electrode.

Figure 6:
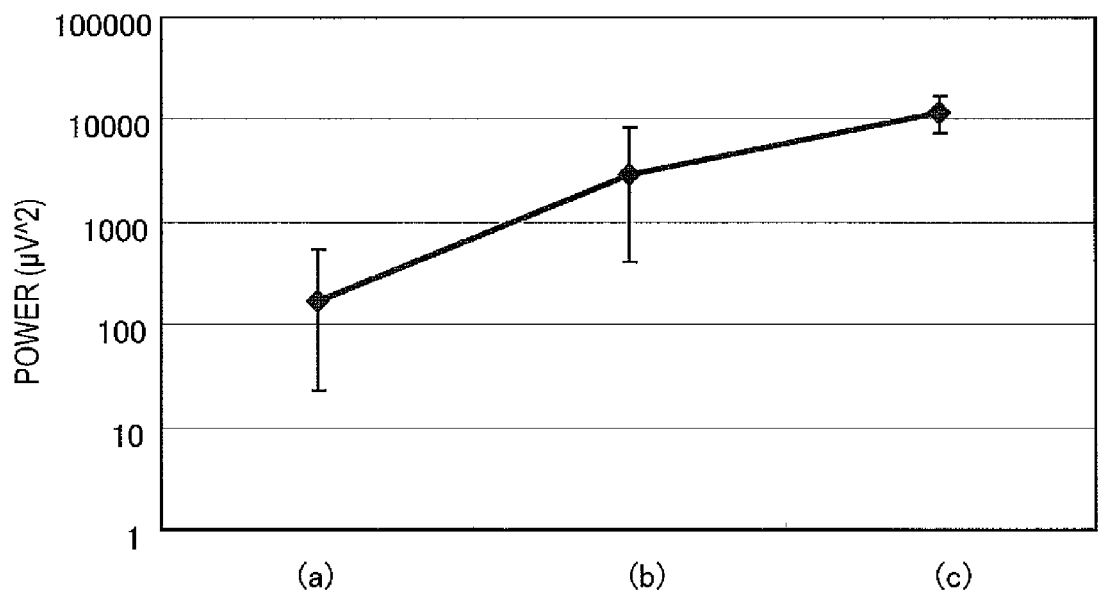

FIG. 6 is a diagram showing an average value of total frequency powers of all test subjects and an extent of variations among all test subjects in the three states of (a), (b), and (c).

FIGS. 7A to 7D are diagrams showing an exemplary manner of wearing a headset-type housing and spatial patterns of insufficient electrodes.

FIG. 8 is a diagram showing methods of insufficiency cause estimation and outputs for different results of insufficient electrode determination.

Figure 9:
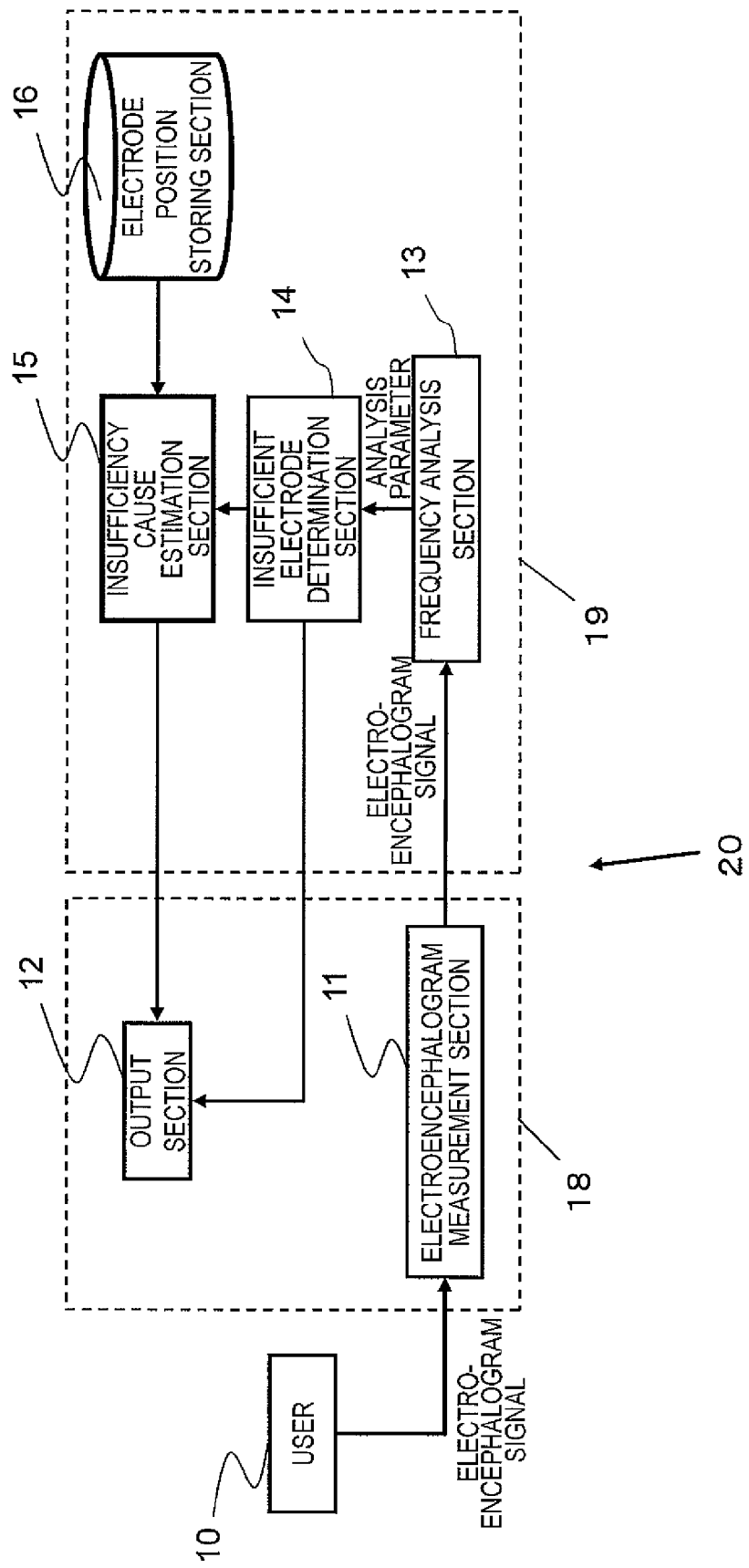

FIG. 9 is a diagram showing the functional block construction of a simplified electroencephalogram measurement system 20 according to Embodiment 1.

Figure 10:
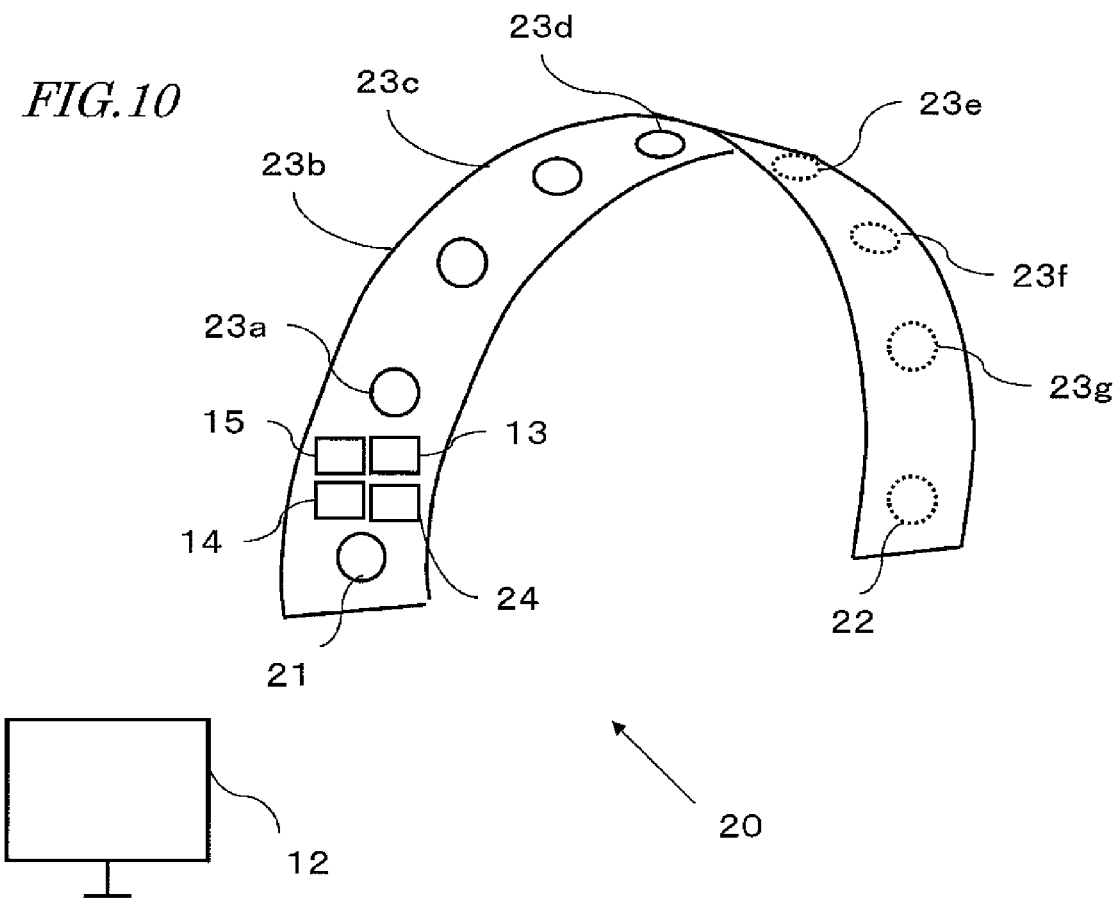

FIG. 10 is a diagram showing an exemplary device shape in the case where the simplified electroencephalogram measurement system 20 is embodied as a headset.

Figure 11:
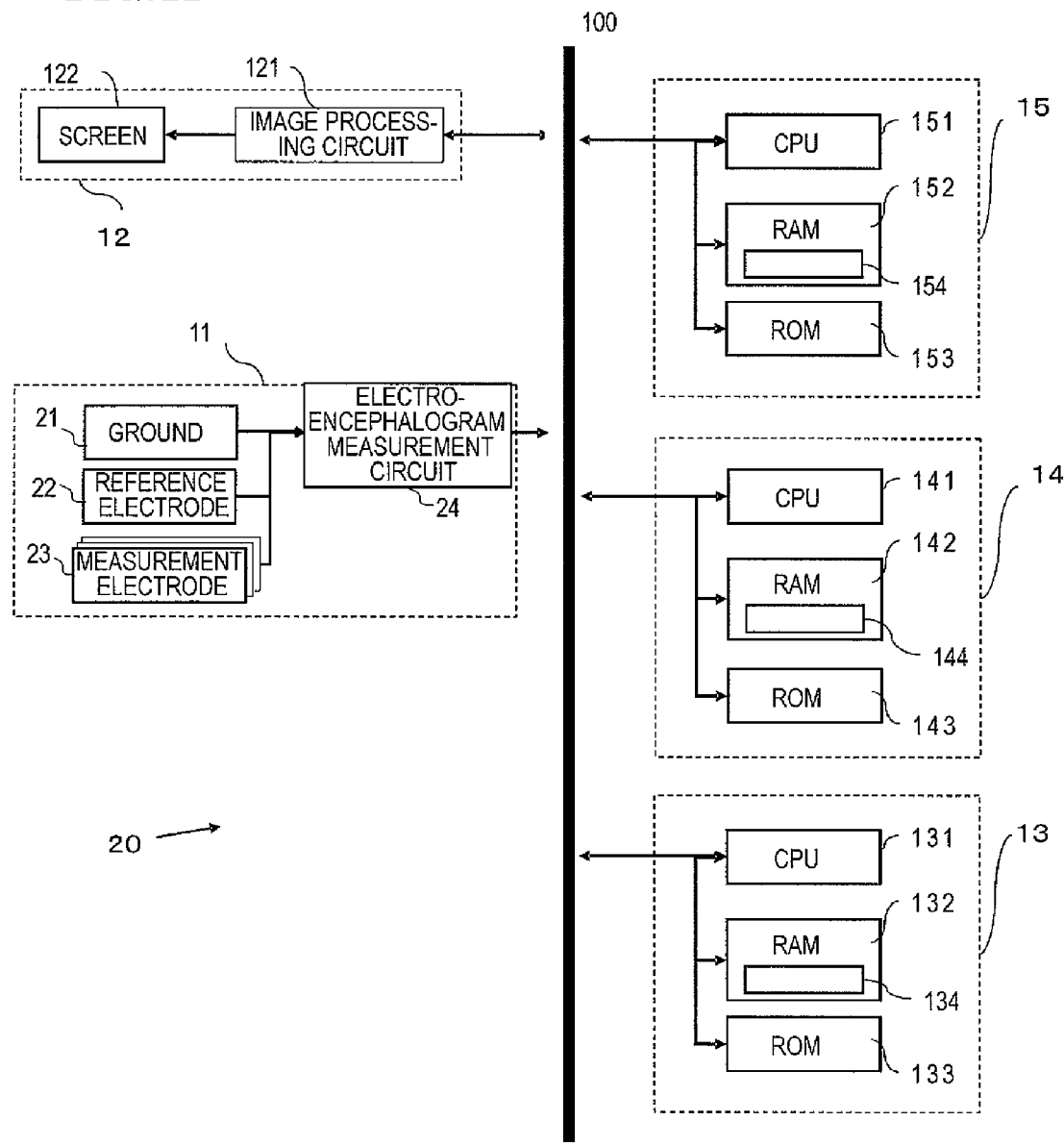

FIG. 11 is a diagram showing an exemplary hardware construction of the simplified electroencephalogram measurement system 20.

Figure 12:
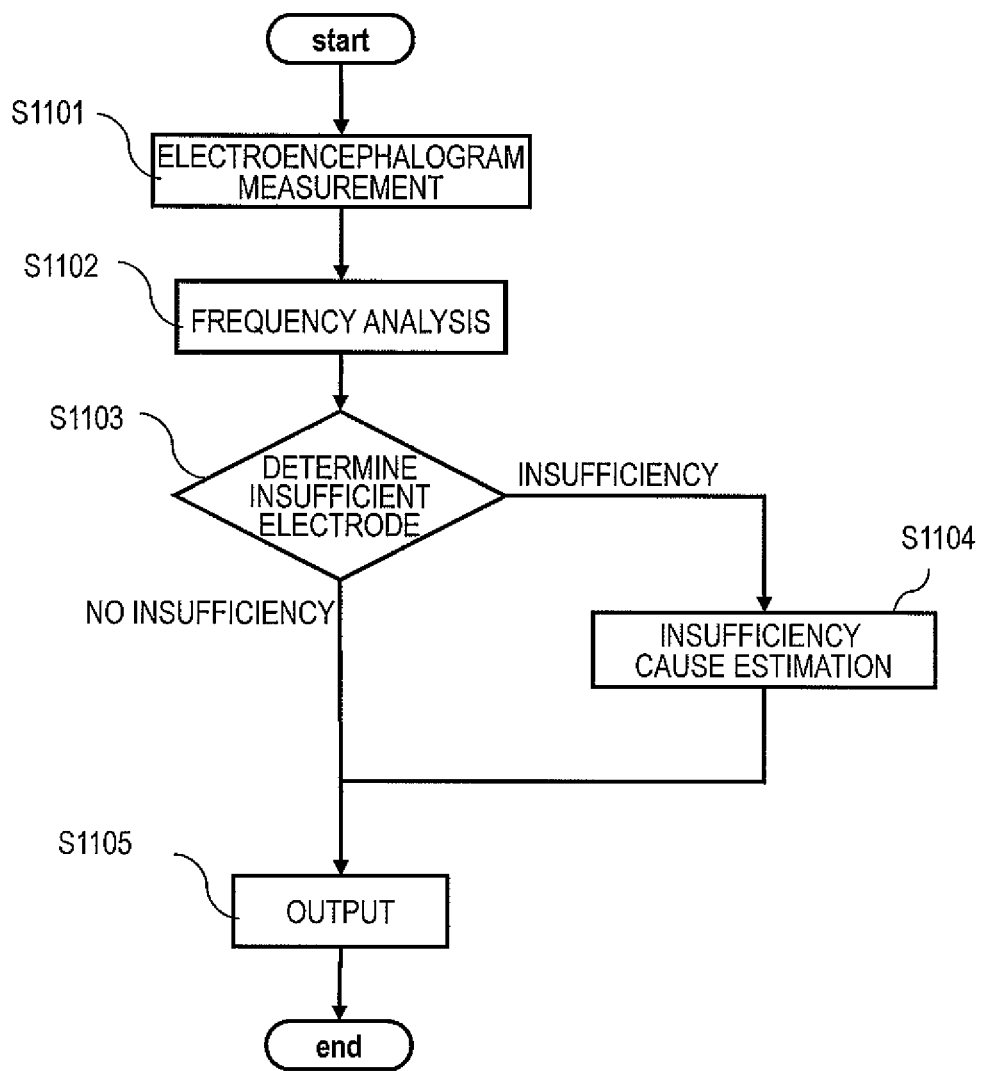

FIG. 12 is a flowchart showing the overall processing by the simplified electroencephalogram measurement system 20.

Figure 13:
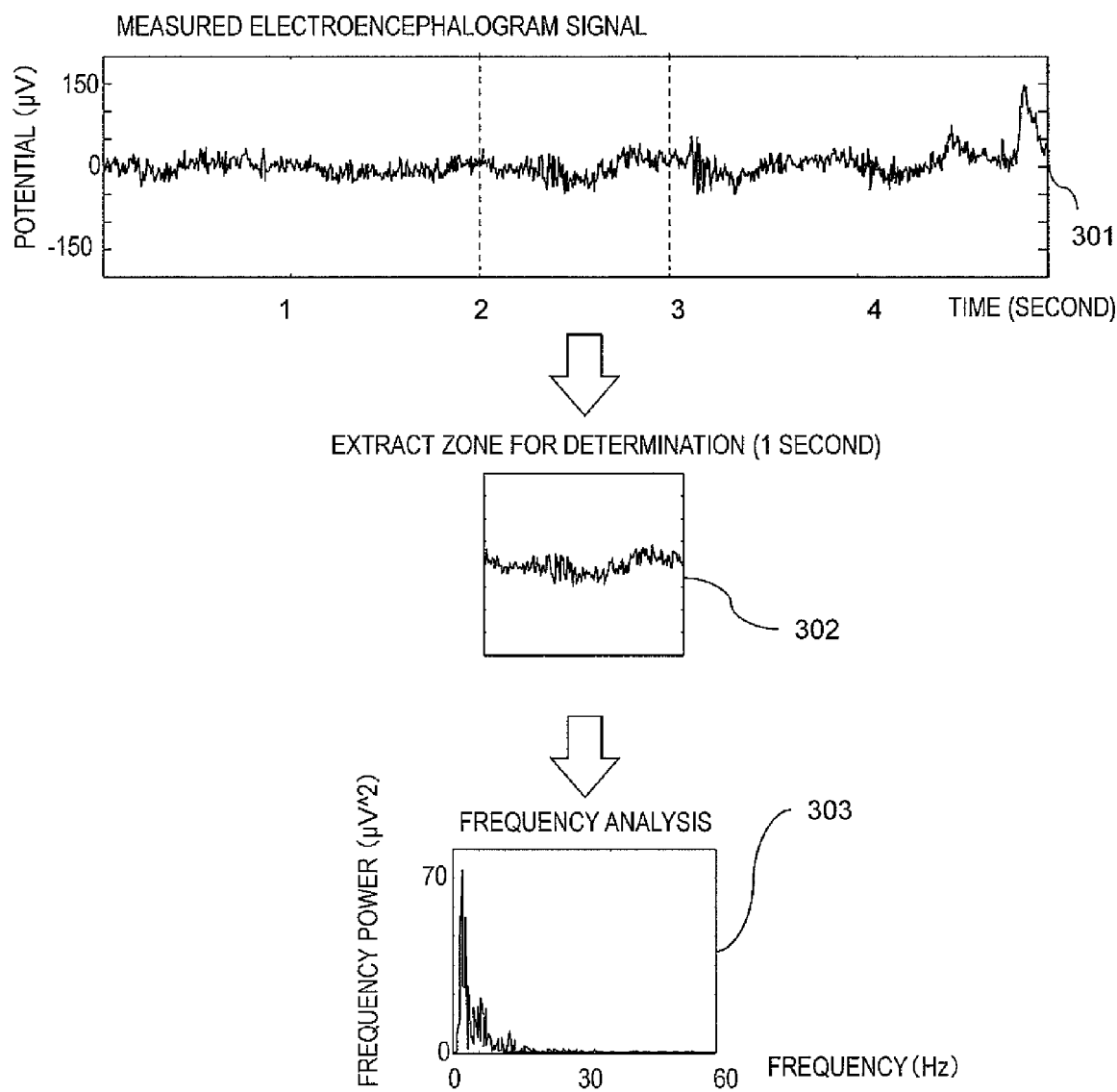

FIG. 13 is a diagram showing an exemplary electroencephalogram waveform for processing by a frequency analysis section 13.

Figure 14:
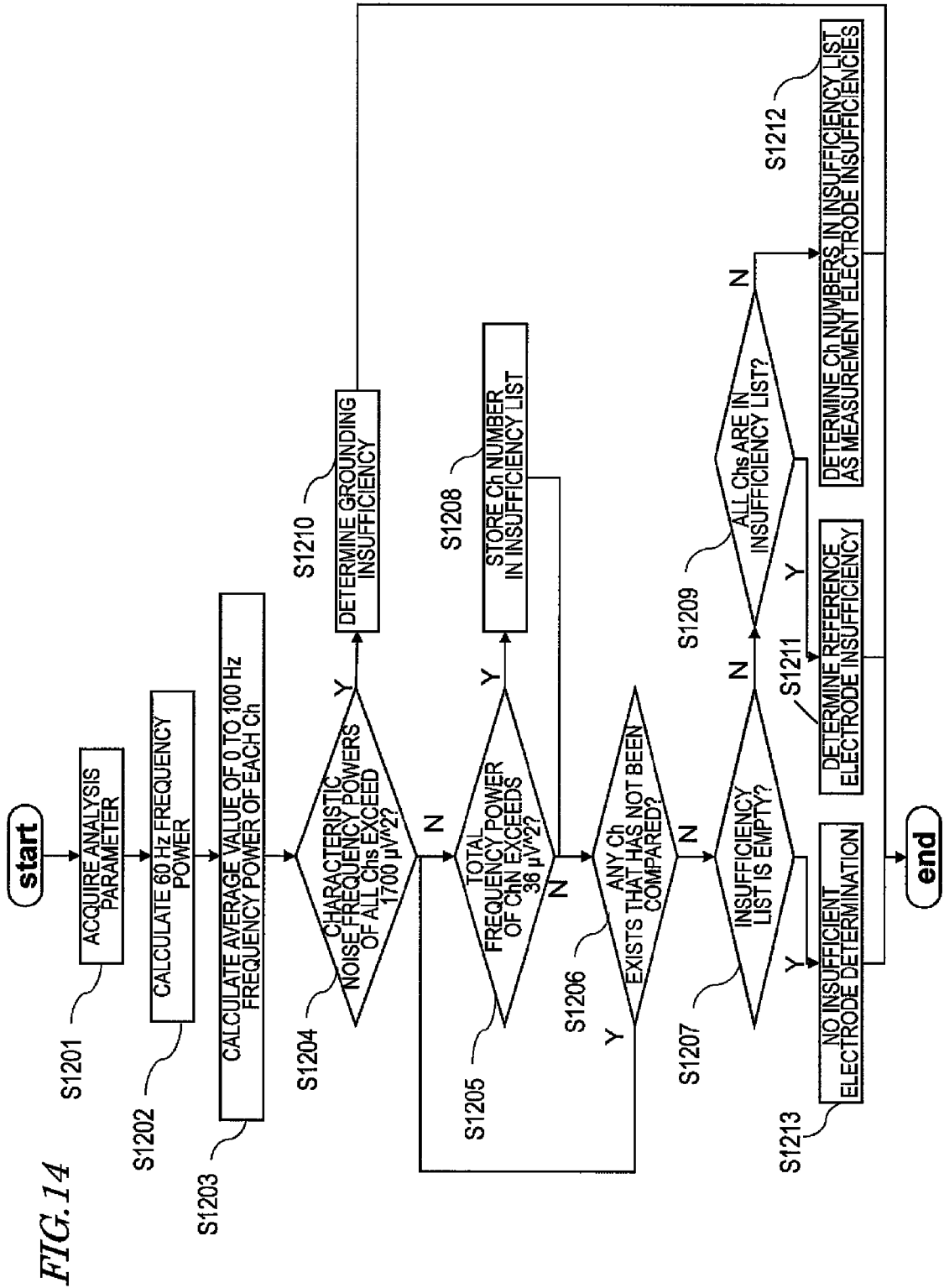

FIG. 14 is a flowchart showing a detailed procedure of processing of a process performed by an insufficient electrode determination section 14 at step S1103 in FIG. 13.

Figure 15:
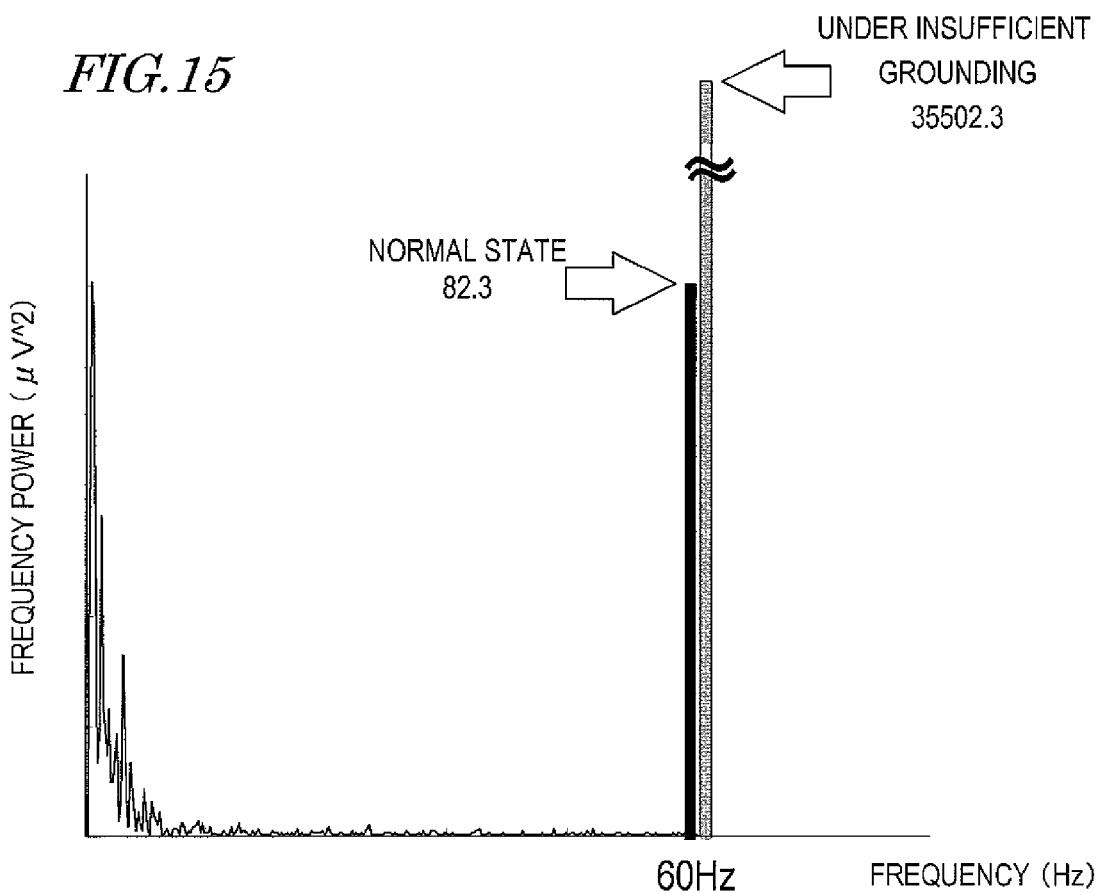

FIG. 15 is an exemplary graph representation of a frequency analysis result in the case where a ground 21 is normally worn (normal state) and a frequency analysis result in the case where the ground is disengaged (insufficient grounding).

Figure 16:
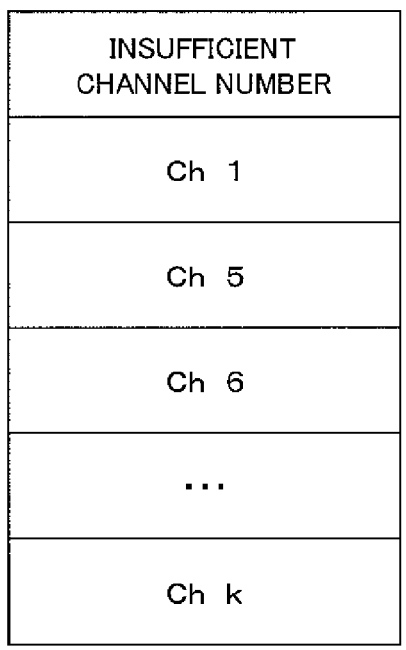

FIG. 16 is a diagram showing examples of insufficient electrodes detected by the insufficient electrode determination section 14.

Figure 17:
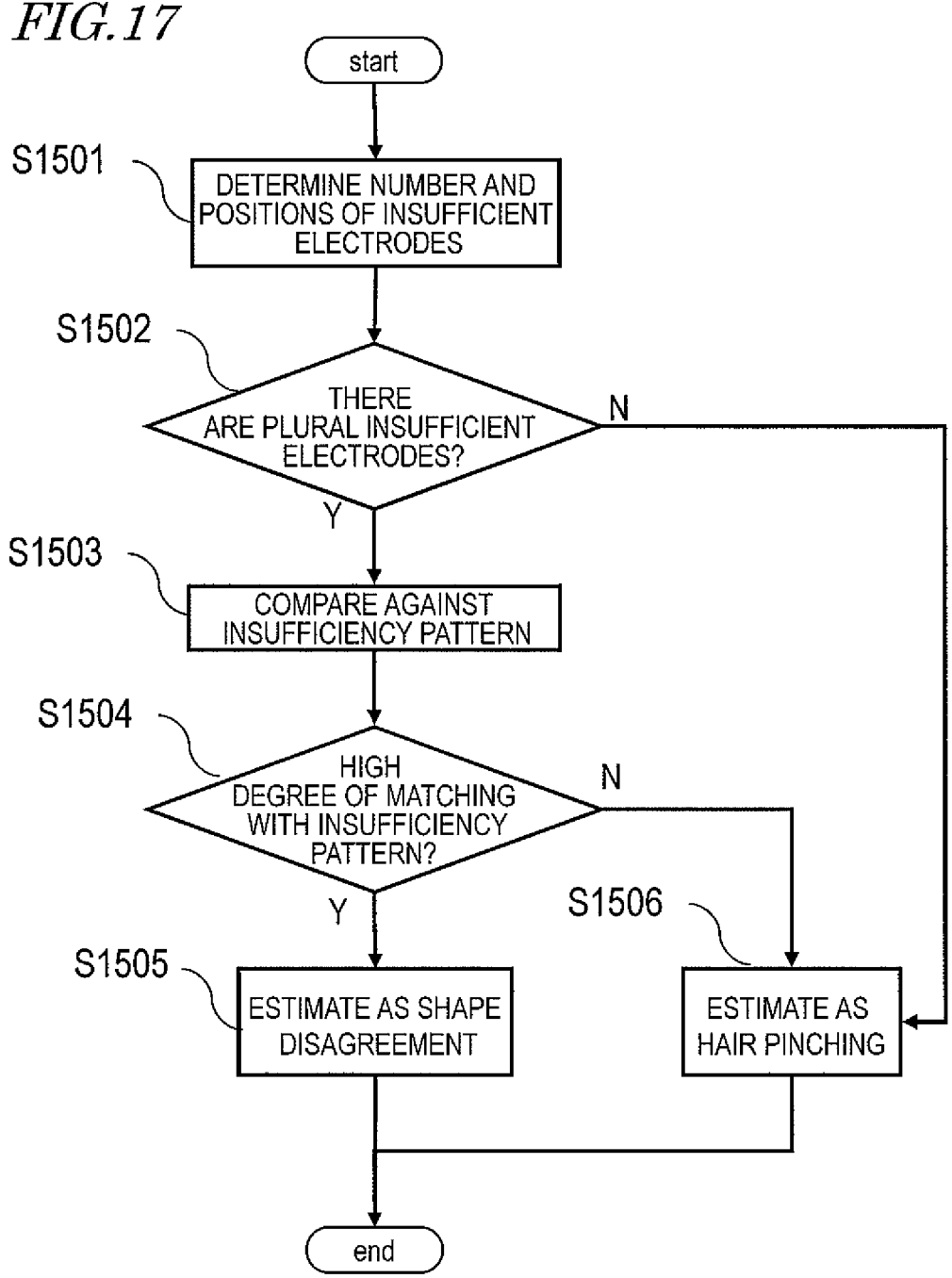

FIG. 17 is a flowchart showing processing by an insufficiency cause estimation section 15.

FIG. 18 is a diagram showing exemplary insufficiency patterns retained in the insufficiency cause estimation section 15.

Figure 19A:
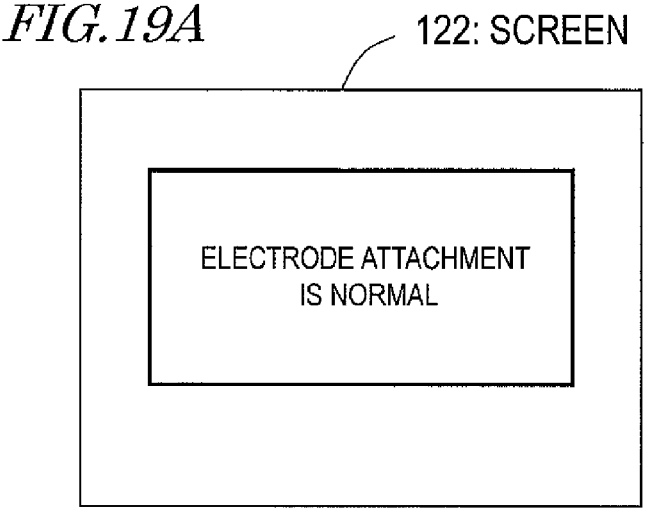
Figure 19B:
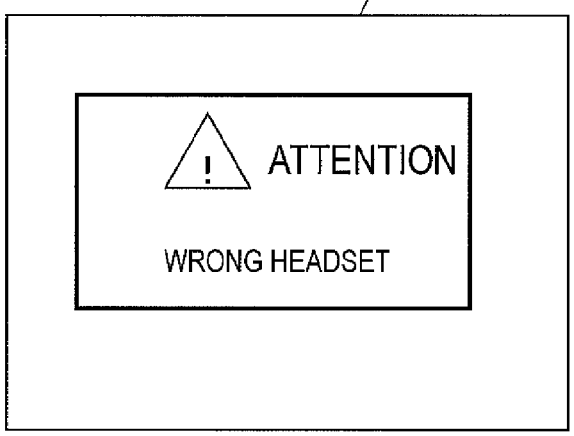
Figure 19C:
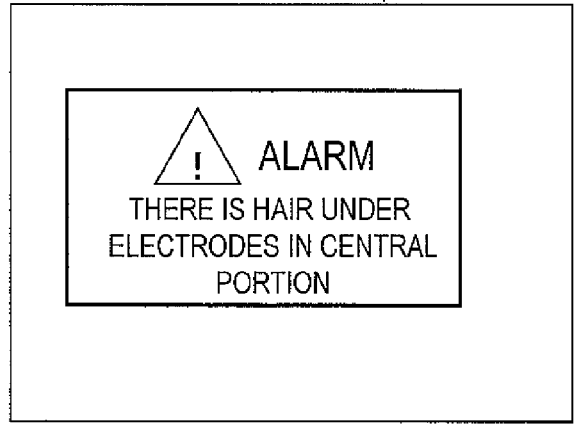

FIGS. 19A to 19C are diagrams showing exemplary results of insufficiency cause estimation.

Figure 20:
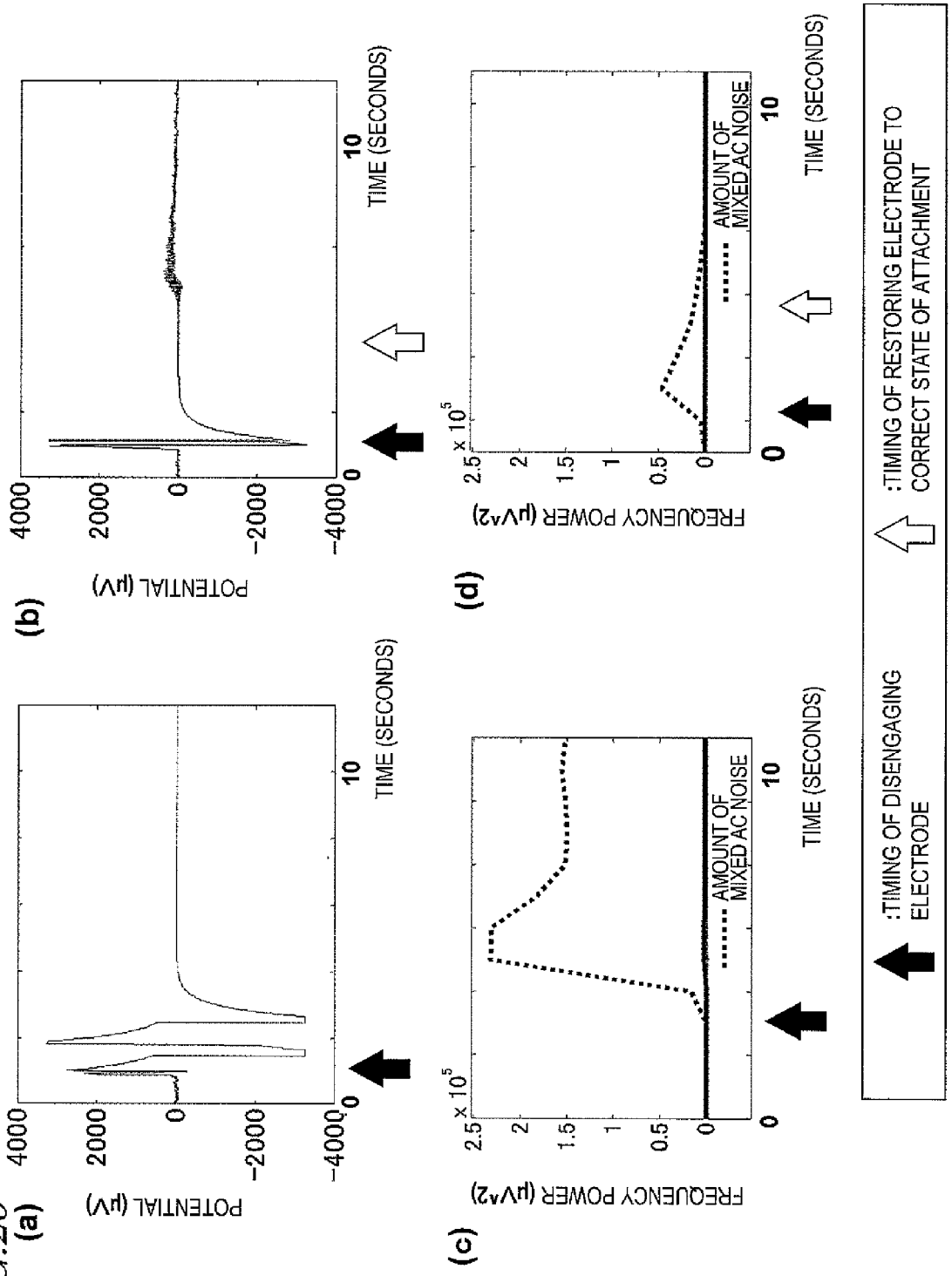

Portions (a) to (d) of FIG. 20 are diagrams showing experimental results.

Figure 21:
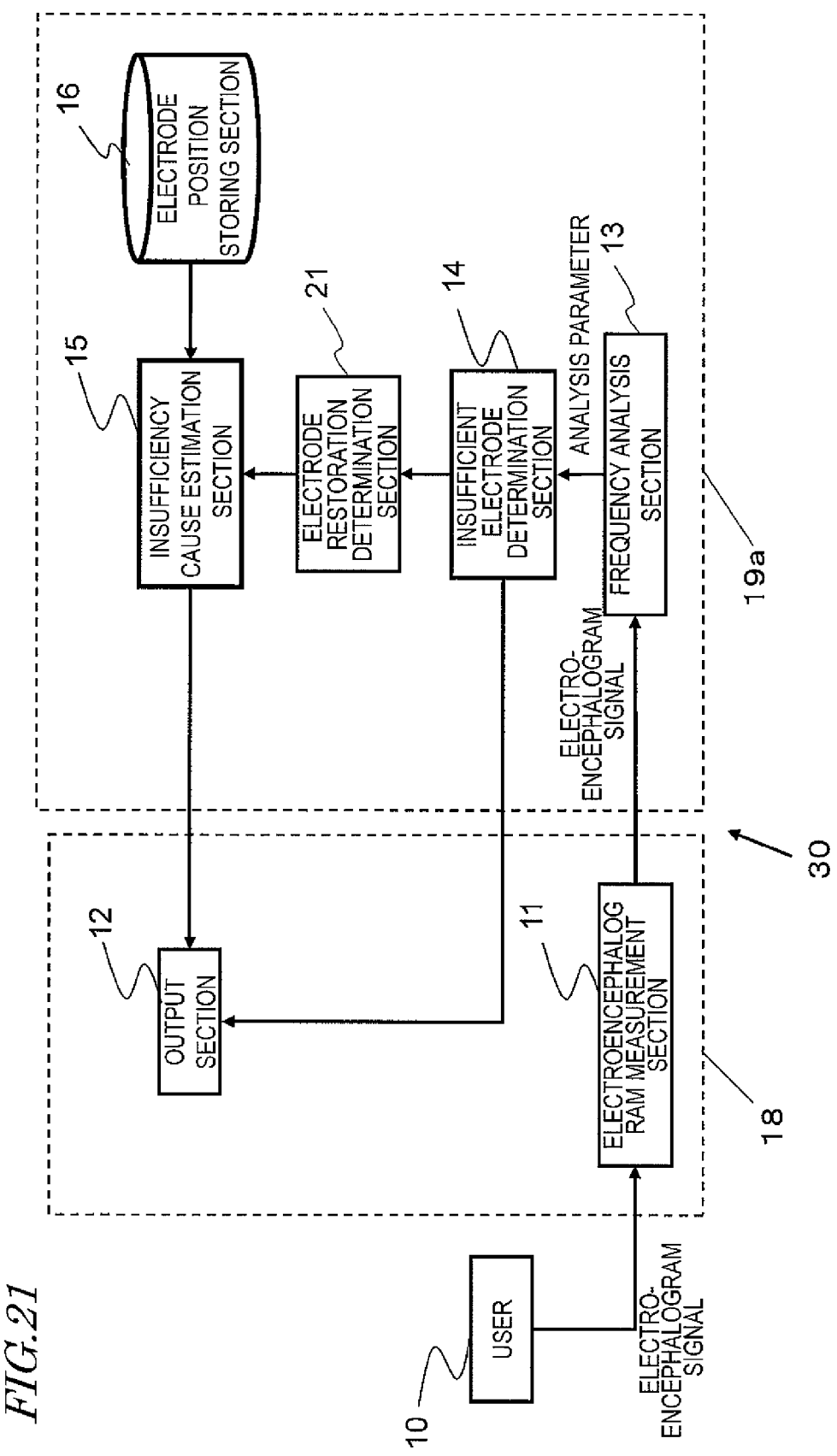

FIG. 21 is a diagram showing a simplified electroencephalogram measurement system 30 according to Embodiment 2.

Figure 22:
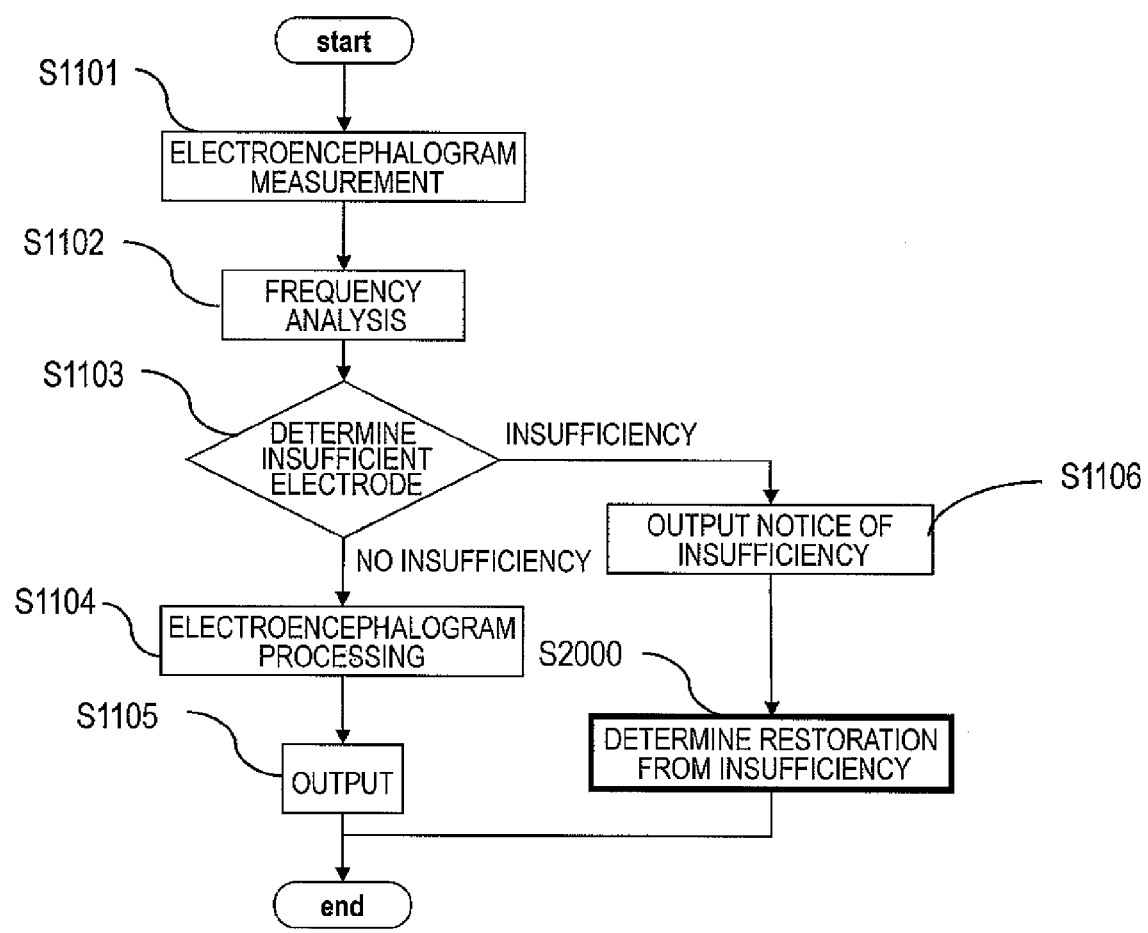

FIG. 22 is a flowchart showing a procedure of processing by a simplified electroencephalogram measurement system 30, which additionally includes processing by an electrode restoration determination section 21.

Figure 23:
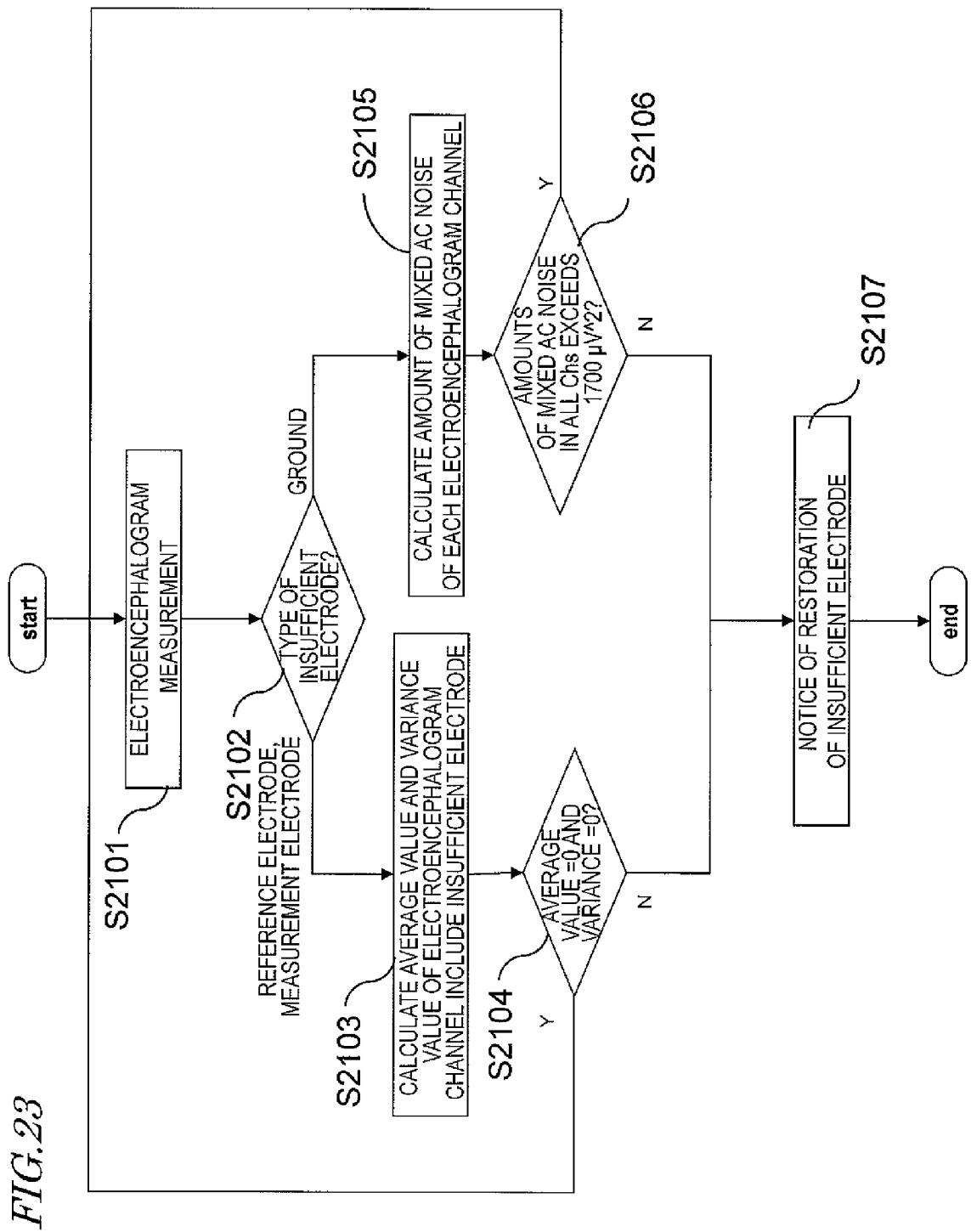

FIG. 23 is a flowchart for describing an electrode restoration determination process (step S2000 in FIG. 20) performed by the electrode restoration determination section 21.

Figure 24:
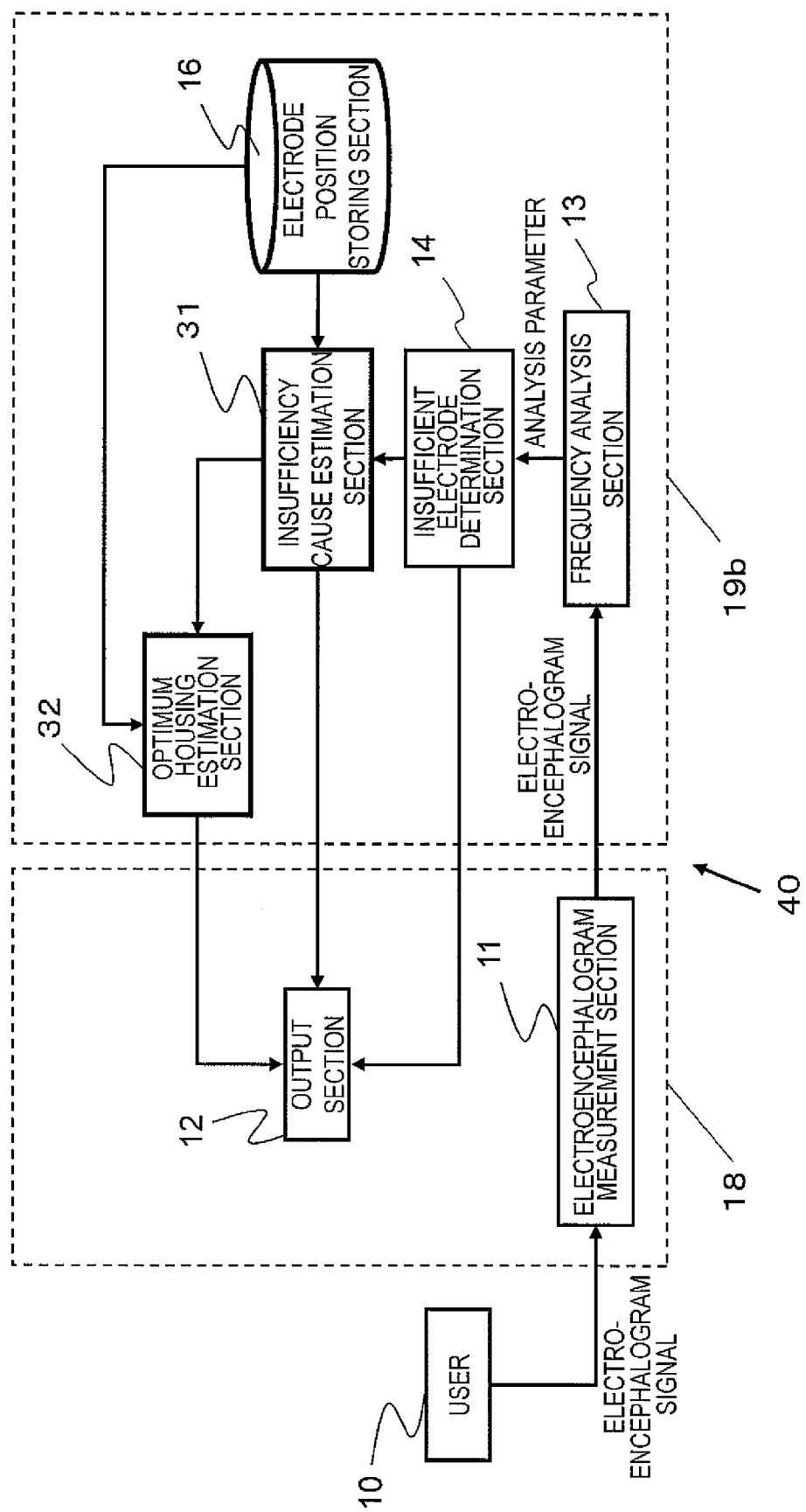

FIG. 24 is a diagram showing the functional block construction of a simplified electroencephalogram measurement system 40 according to Embodiment 3.

Figure 25:
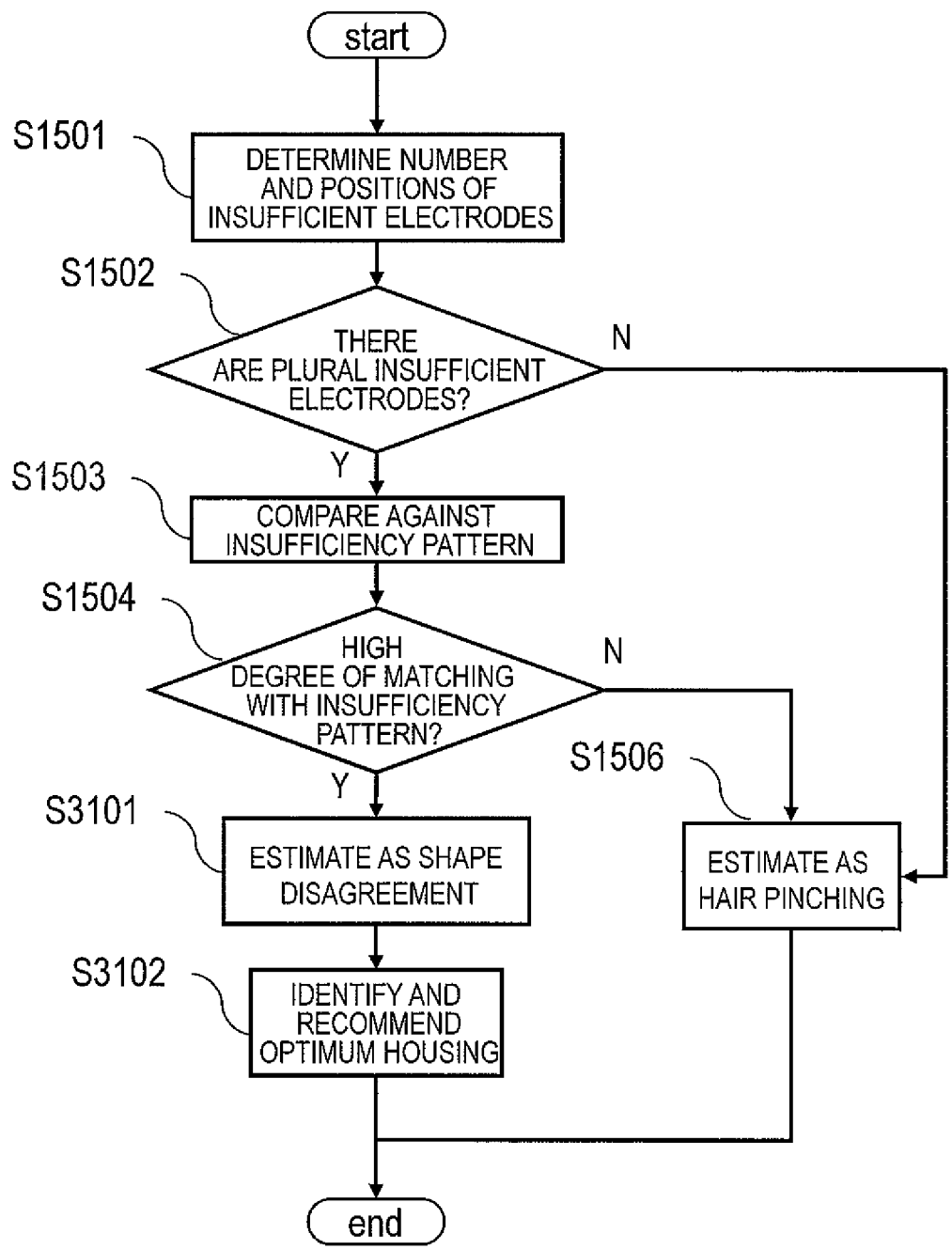

FIG. 25 is a flowchart showing processing by an insufficiency cause estimation section 31 and an optimum housing estimation section 32 according to Embodiment 3.

Figures 26, 27:
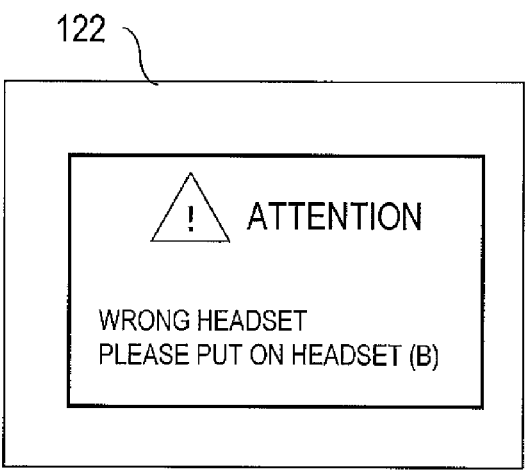

FIG. 26 is a diagram showing examples of information concerning a plurality of housing shapes retained in the optimum housing recommendation section 32.

FIG. 27 is a diagram showing an exemplary output of a result of optimum housing estimation.

DETAILED DESCRIPTION

The techniques of the aforementioned conventional approaches are all directed to the detection of insufficient wearing of a single electrode, in the electroencephalogram measurements in a daily-life environment. Therefore, at the present time, it has been impossible to identify causes of insufficiency ("insufficiency causes"). The user needs to search through a number of electrodes in order to identify an insufficiency cause, which has been a trouble to the user. The problems of the respective techniques described in Patent Documents 1 to 4 will be described in detail below.

Patent Document 1 and Patent Document 2 are not tailored for the detection of an insufficient electrode in an environment where the state of electrode attachment keeps changing, and have difficulties in identifying the electrode that has become insufficient, not mention the impossibility of identifying a cause of insufficiency for an insufficient electrode.

In the approach of Patent Document 1, it is necessary to stop the electroencephalogram measurement before measuring the contact resistance, and reconciliation between electroencephalogram measurement and contact resistance is not an issue here. This approach is based the premise that the state of contact of an electrode will not change, contemplating that the contact resistance is to be measured only at the beginning of the measurement. However, the state of electrode attachment will change over time in a daily-life environment, and thus the frequency with which to confirm the state of attachment should increase. The need to stop the electroencephalogram measurement each time before a contact resistance measurement will present considerable inconvenience.

In the approach of Patent Document 2, it is determined as to whether an electrode is in contact with the skin or not. Therefore, no consideration is given to the insufficiencies concerning the state of contact of the electrode, e.g., shifting of the electrode that may occur in response to the user's motion, or changes in the pressure from the electrode.

On the other hand, in Patent Document 3, insufficiencies of electroencephalogram measurement can also be detected even in an environment where the state of attachment may change. However, it is still impossible to identify which electrode is suffering from insufficient wearing. Therefore, in Patent Document 3, too, it is impossible to identify an insufficiency cause which exists for an insufficient electrode.

In Patent Document 4, in the case where insufficiency of wearing has been detected for a plurality of combinations of electrodes, an electrode that exists in common among the combinations of electrodes suffering from insufficiencies of wearing is searched for; thus, the insufficient electrode is identified. However, Patent Document 4 does not address the case where more than one electrode is included in common among the combinations of electrodes suffering from insufficiencies. While capable of identifying an insufficient electrode when it is the only insufficient electrode that is present, the system of Patent Document 4 does not assume the existence of a plurality of insufficient electrodes. When a plurality of insufficient electrodes exist, the operation principles of the system of Patent Document 4 do not allow each one of them to be identified. Consequently, it is impossible to identify an insufficiency cause that exists for each insufficient electrode.

As described above, when measuring an electroencephalogram with dry electrodes, the user's trouble associated with the handling of paste is reduced, but electrode shifting and electrode disengagement may occur due to user motions. Moreover, when an electroencephalogram is to be measured with electrodes being incorporated in a housing of e.g. an HMD or a headset, the electrodes need to be properly worn at predetermined positions. Since the housing would have a relatively high rigidity, the electrode positions would not be able to be flexibly adjusted. Therefore, electrode disengagement due to a disagreement between the head shape and the housing shape will be particularly problematic. In addition, at any haired site, the task of digging into the hair and attaching an electrode by himself or herself can be difficult, and it is expected that "hair pinching" may occur, i.e., hair being caught between the electrode and the skin, even when the electrode and the head are otherwise in contact. Since oftentimes an electroencephalogram is measured on a head that has hair on it, hair pinching is considered to occur rather frequently.

Such insufficiencies may occur each by a different cause, by itself or concurrently in combination, and it is impossible for the user himself or herself to identify which cause is hindering stable electroencephalogram measurements. Therefore, the user is compelled to make hunt-down efforts with respect to such insufficiencies. This may result, for example, in an improper remedy being taken for hair pinching, e.g., by shifting the angle of wearing the housing, and thus is troublesome to the user. In particular, when various insufficiencies have concurrently occurred for a plurality of electrodes, it is very difficult for the user to eliminate each insufficiency cause one by one.

Nonetheless, it is anticipated that future advances may reduce the extra expenses and processes and alleviate the above problems.

One non-limiting, and exemplary embodiment provides an electroencephalogram measurement system comprising: an electroencephalogram measurement section having a plurality of electrodes being disposed in one housing, the plurality of electrodes including a reference electrode, measurement electrodes and a ground, for measuring an electroencephalogram signal between the reference electrode and a measurement electrode on the basis of the ground, the plurality of electrodes constituting a plurality of electroencephalogram measurement channels, such that each electroencephalogram measurement channel is defined by at least the reference electrode and a measurement electrode; an electrode position storing section for storing positions at which the plurality of electrodes respectively come in contact with a user when the user wears the electroencephalogram measurement section; a frequency analysis section for analyzing a frequency power of the electroencephalogram signal measured by the electroencephalogram measurement section with respect to each electroencephalogram measurement channel; an insufficient electrode determination section for distinguishing whether a state of attachment of each electrode is sufficient or not by comparing the frequency power analyzed by the frequency analysis section against a predetermined first threshold value; and an insufficiency cause estimation section for: determining the number of insufficient electrodes distinguished as insufficiently worn at the insufficient electrode determination section; determining a position at which each insufficient electrode determined as insufficiently worn at the insufficient electrode determination section is in contact with the user, by referring to the positions of the plurality of electrodes stored in the electrode position storing section; and estimating a cause for the insufficient state of attachment of the insufficient electrode or electrodes that corresponds to the determined number of insufficient electrodes and position of each insufficient electrode, by referring to insufficiency pattern data defining associations between the number of insufficient electrodes, the position at which each insufficient electrode comes in contact with the user, and causes for the insufficient state of attachment of the insufficient electrode or electrodes.

The insufficiency pattern data may define the associations so that, when the number of insufficient electrodes is greater than a second threshold value and there are contiguous insufficient electrodes adjoining one another, the cause for the insufficient state of attachment of the insufficient electrode or electrodes is associated with disagreement between a head shape of the user and shape of the housing of the electroencephalogram measurement section.

The insufficient electrode determination section may extract a noise amount parameter from the result of the frequency power analysis, and if the noise amount parameter has a value exceeding a predetermined third threshold value, determines that the ground is insufficiently worn.

The insufficient electrode determination section may further extract a total frequency power parameter from the result of the frequency power analysis, and if the total frequency power parameter has a value exceeding a predetermined second threshold value, determine that the reference electrode or a measurement electrode is insufficiently worn.

The electroencephalogram measurement section may use a plurality of sets of electrodes each including a ground, a reference electrode, and a measurement electrode, to measure an electroencephalogram signal with each set; the frequency analysis section may perform a frequency power analysis of each electroencephalogram signal; and the insufficient electrode determination section may extract a noise amount parameter from a result of the frequency power analysis of each electroencephalogram signal, and if all of the noise amount parameters have values exceeding a predetermined third threshold value, determine that the ground is insufficiently worn, and extract a total frequency power parameter from the result of the frequency power analysis of each electroencephalogram signal, and if all of the total frequency power parameters have values exceeding a predetermined second threshold value, determine that the reference electrode is insufficiently worn, or if some of the extracted total frequency power parameters have values exceeding the fourth threshold value, determine that a measurement electrode is insufficiently worn.

The electroencephalogram measurement section may measure a first potential difference and a second potential difference, the first potential difference being a potential difference between the ground and the reference electrode and the second potential difference being a potential difference between the ground and the measurement electrode, and measure the electroencephalogram signal based on a difference between the second potential difference and the first potential difference.

A noise being steadily mixed from an external environment at a previously identified frequency may be superposed on the electroencephalogram signal; and from the result of the frequency analysis, the insufficient electrode determination section may extract a frequency power of the noise as the noise amount parameter.

The previously identified frequency may be a frequency of a commercial-power noise of a device which is in the external environment.

The electroencephalogram measurement system may further comprise an output section for outputting a result of estimation by the insufficient electrode estimation section, and, if no insufficient electrode is detected by the insufficient electrode determination section, the output section may output an indication of a sufficient state of attachment.

The electroencephalogram measurement system may further comprise an output section for outputting a result of estimation by the insufficient electrode estimation section, and, if any insufficient electrode is detected by the insufficient electrode determination section, the output section may output an indication of a position of the insufficient electrode.

When the number of insufficient electrodes distinguished as insufficiently worn at the insufficient electrode determination section is greater than a predetermined second threshold value, the insufficiency cause estimation section may estimate the cause for the insufficient state of attachment of the insufficient electrode or electrodes to be disagreement between a head shape of the user and shape of the housing of the electroencephalogram measurement section if a correlation coefficient between a position or positions of the insufficient electrode or electrodes determined as insufficiently worn and a position or positions of an insufficient electrode or electrodes in the insufficiency pattern data exceeds a predetermined threshold value.

The electroencephalogram measurement system may further comprise an electrode restoration determination section for determining, based on a signal measured by using an insufficient electrode which is determined as insufficiently worn, whether the insufficiency in the state of attachment of the insufficient electrode has been eliminated or not, and, when the insufficient electrode determined as insufficiently worn is the ground, the electrode restoration determination section may extract the noise amount parameter from the result of the frequency power analysis of the signal as measured by using the insufficient electrode, and, if the noise amount parameter has a value exceeding a predetermined third threshold value, the electrode restoration determination section may determine that the insufficiency in the state of attachment of the insufficient electrode has not been eliminated, or if the noise amount parameter does not have a value exceeding a predetermined third threshold value, the electrode restoration determination section may determine that the insufficiency in the state of attachment of the insufficient electrode has been eliminated.

The electroencephalogram measurement system may further comprise an optimum housing recommendation section for, when cause for the insufficient state of attachment is estimated by the insufficiency cause estimation section to be disagreement between the head shape and the shape of the housing, recommending an optimum housing based on information of disagreement in shape and the shape of the current housing.

Another exemplary electroencephalogram measurement system according to the present disclosure is an electroencephalogram measurement system comprising: an electroencephalogram measurement section having a plurality of electrodes being disposed in one housing, the plurality of electrodes including a reference electrode and measurement electrodes, for measuring an electroencephalogram signal of a user between the reference electrode and a measurement electrode, the plurality of electrodes constituting a plurality of electroencephalogram measurement channels, such that each electroencephalogram measurement channel is defined by at least the reference electrode and a measurement electrode; a frequency analysis section for analyzing a frequency power of the electroencephalogram signal measured by the electroencephalogram measurement section with respect to each electroencephalogram measurement channel; an insufficient electrode determination section for distinguishing whether a state of attachment of each electrode is sufficient or not by comparing the frequency power analyzed by the frequency analysis section against a predetermined first threshold value; and an insufficiency cause estimation section for estimating a cause for the insufficient state of attachment of the insufficient electrode or electrodes, wherein, when the number of insufficient electrodes distinguished as insufficiently worn at the insufficient electrode determination section is equal to or less than a predetermined second threshold value, the insufficiency cause estimation section estimates the cause to be existence of hair of the user between a head of the user and the insufficient electrode or electrodes distinguished as insufficiently worn.

Still another exemplary electroencephalogram measurement system according to the present disclosure is an electroencephalogram measurement system comprising: a frequency analysis section for analyzing a frequency power of an electroencephalogram signal measured by an electroencephalogram measurement section having a plurality of electrodes being disposed in one housing, the plurality of electrodes including a reference electrode, measurement electrodes and a ground, the electroencephalogram measurement section measuring an electroencephalogram signal between the reference electrode and a measurement electrode on the basis of the ground, the plurality of electrodes constituting a plurality of electroencephalogram measurement channels such that each electroencephalogram measurement channel is defined by at least the reference electrode and a measurement electrode, the frequency power of the electroencephalogram signal being analyzed with respect to each electroencephalogram measurement channel; an insufficient electrode determination section for distinguishing whether a state of attachment of each electrode is sufficient or not by comparing the frequency power analyzed by the frequency analysis section against a predetermined first threshold value; and an insufficiency cause estimation section for determining the number of insufficient electrodes distinguished as insufficiently worn at the insufficient electrode determination section and a position at which each insufficient electrode is in contact with the user, and estimating a cause for the insufficient state of attachment of the insufficient electrode or electrodes that corresponds to the determined number and positions of insufficient electrodes, by referring to insufficiency pattern data defining associations between the number of insufficient electrodes, the position at which each insufficient electrode comes in contact with the user, and causes for the insufficient state of attachment, wherein the insufficiency cause estimation section determines the position at which each insufficient electrode is in contact with the user by referring to positions of the plurality of electrodes stored in an electrode position storing section for storing positions at which the plurality of electrodes respectively come in contact with a user when the user wears the electroencephalogram measurement section.

An exemplary electroencephalogram measurement method according to the present disclosure is an electroencephalogram measurement method comprising: an electroencephalogram measurement step of measuring an electroencephalogram signal of a user by using a plurality of electrodes disposed in one housing, the plurality of electrodes including a reference electrode, measurement electrodes and a ground, the electroencephalogram signal being measured between the reference electrode and a measurement electrode on the basis of the ground, the plurality of electrodes constituting a plurality of electroencephalogram measurement channels, such that each electroencephalogram measurement channel is defined by at least the reference electrode and a measurement electrode; a frequency analysis step of analyzing a frequency power of the electroencephalogram signal measured in the electroencephalogram measurement step with respect to each electroencephalogram measurement channel; an insufficient electrode determination step of distinguishing whether a state of attachment of each electrode is sufficient or not by comparing the frequency power analyzed in the frequency analysis step against a predetermined first threshold value; a determination step of determining the number of insufficient electrodes distinguished as insufficiently worn at the insufficient electrode determination step, and determining a position at which each insufficient electrode determined as insufficiently worn at the insufficient electrode determination step is in contact with the user by referring to information of positions at which the plurality of electrodes respectively come in contact with the user when the user wears the housing at the electroencephalogram measurement step; and an insufficiency cause estimation step of estimating a cause for the insufficient state of attachment of the insufficient electrode or electrodes that corresponds to the determined number of insufficient electrodes and position of each insufficient electrode, by referring to insufficiency pattern data defining associations between the number of insufficient electrodes, the position at which each insufficient electrode comes in contact with the user, and causes for the insufficient state of attachment.

A exemplary computer program according to the present disclosure is a computer program, stored on a non-transitory computer-readable storage medium, to be executed by a computer for electroencephalogram measurement, wherein the computer program causes the computer to execute the steps of: an electroencephalogram measurement step of measuring an electroencephalogram signal of a user by using a plurality of electrodes disposed in one housing, the plurality of electrodes including a reference electrode, measurement electrodes and a ground, the electroencephalogram signal being measured between the reference electrode and a measurement electrode on the basis of the ground, the plurality of electrodes constituting a plurality of electroencephalogram measurement channels, such that each electroencephalogram measurement channel is defined by at least the reference electrode and a measurement electrode; a frequency analysis step of analyzing a frequency power of the electroencephalogram signal measured in the electroencephalogram measurement step with respect to each electroencephalogram measurement channel; an insufficient electrode determination step of distinguishing whether a state of attachment of each electrode is sufficient or not by comparing the frequency power analyzed in the frequency analysis step against a predetermined first threshold value; a determination step of determining the number of insufficient electrodes distinguished as insufficiently worn at the insufficient electrode determination step, and determining a position at which each insufficient electrode determined as insufficiently worn at the insufficient electrode determination step is in contact with the user by referring to information of positions at which the plurality of electrodes respectively come in contact with the user when the user wears the housing at the electroencephalogram measurement step; and an insufficiency cause estimation step of estimating a cause for the insufficient state of attachment of the insufficient electrode or electrodes that corresponds to the determined number of insufficient electrodes and position of each insufficient electrode, by referring to insufficiency pattern data defining associations between the number of insufficient electrodes, the position at which each insufficient electrode comes in contact with the user, and causes for the insufficient state of attachment.

According to the present disclosure, in an electroencephalogram measurement system in which electrodes incorporated in one housing are worn on the head of a user, at least one parameter of either a total frequency power or a noise amount is extracted from the measured potential waveform, and through a comparison of the parameter value against a predetermined threshold value, an insufficient electrode(s) is detected. Then, an insufficiency cause is estimated from the number and spatial pattern of insufficient electrodes, and is output to the user. This makes it possible to reduce hunt-down efforts for insufficiencies of electrode attachment, and realize stable electroencephalogram measurement with ease.

The inventors have developed, in a system where a housing having electrodes incorporated therein is worn on a head to measure an electroencephalogram, a method for simplified electrode attachment, involving estimating an insufficiency cause from a pattern of spatial positions of insufficient electrodes, and recommending a proper remedy for each cause. This is unprecedentedly realized via insufficient electrode determination based on characteristic signals which are measured at insufficient electrodes, which have been, discovered by the inventors.

First, the principles of the present disclosure concerning insufficient electrode determination will be described in detail, followed by a description of a method of insufficiency cause estimation utilizing results of insufficient electrode determination. Thereafter, embodiments of the present disclosure will be described.

(Method of insufficient electrode determination)

In regard to cases where a plurality of types of electrodes ("measurement electrode", "reference electrode", and "ground") of an electroencephalograph respectively suffer from insufficiencies, the inventors have conducted an experiment to examine what sort of influence is exerted on the electroencephalogram waveform in each case. As a result of this, the inventors have found this characteristic feature: depending on what kind of and how much noise is mixed and the type of insufficiency, it is possible to identify a particular electrode type which has become insufficient, by merely relying on the electroencephalogram waveform.

As used herein, a "measurement electrode" is an electrode which is worn at a site where an encephalic activity to be measured is occurring. A measurement electrode is also referred to as a recording electrode.

A "reference electrode" is an electrode which is worn at a site that undergoes little change in potential due to encephalic activities. The reference electrode is worn at an ear periphery (an earlobe or mastoid) or the like, for example. The reference electrode is also referred to as an indifferent electrode.

"Ground" refers to an electrode which is worn for the purpose of removing in-phase noises through differential amplification. The ground is set at a place which is not susceptible to the influences of potential fluctuations associated with encephalic activities. For example, it may be at a nose pad position in the case of an HMD, or in an ear periphery in the case of a headset. The method of noise removal will be described later.

Hereinafter, an exemplary construction of an electroencephalograph having the aforementioned electrodes ("measurement electrode", "reference electrode", and "ground") will be described. Thereafter, details of experiments performed by the inventors and novel findings obtained from the experimental results will be described.

Figure 1:
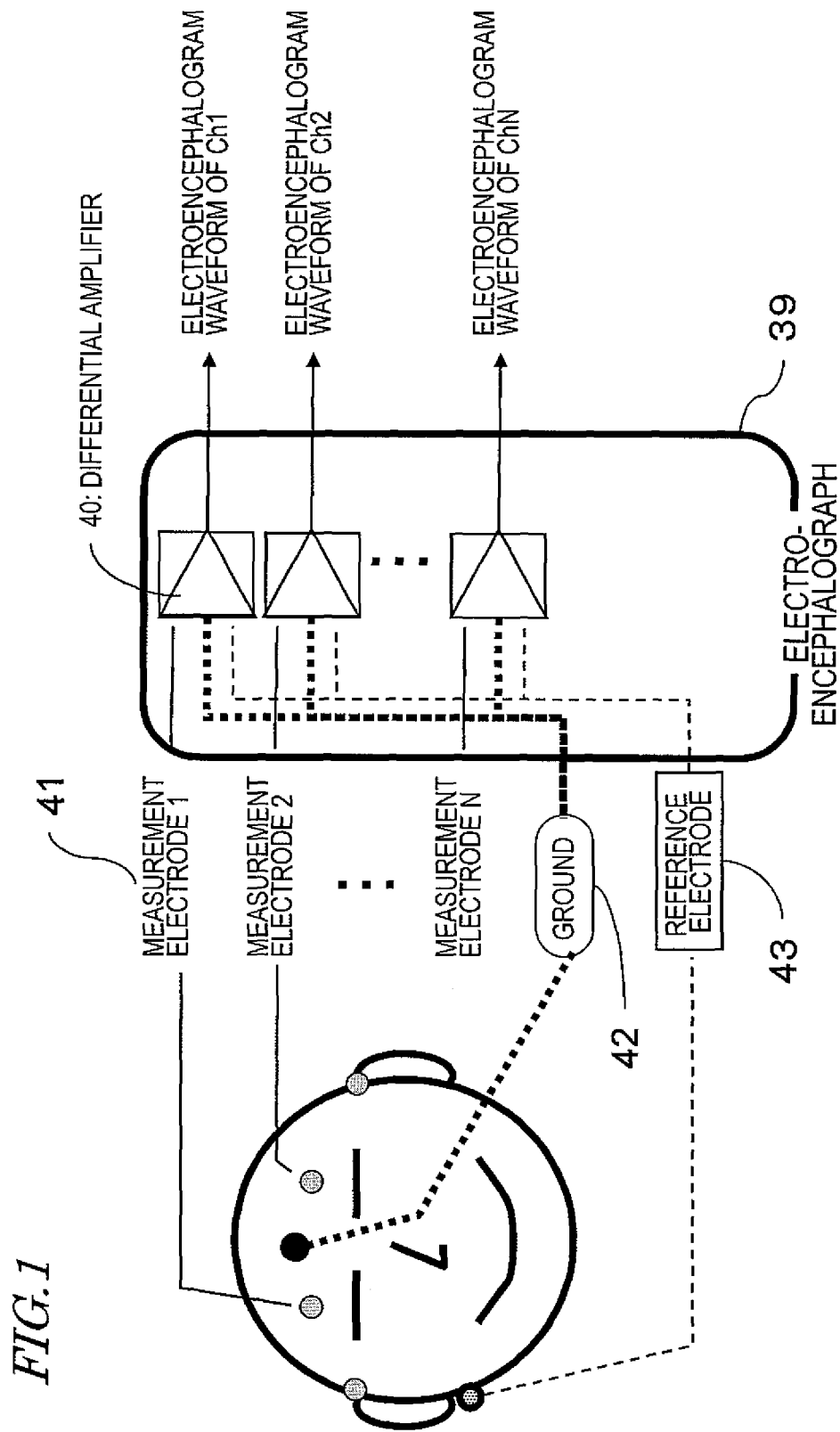
FIG. 1 is a diagram showing the construction of an electrode electroencephalograph 39 having a plurality of types of electrodes 41 to 43.

FIG. 1 shows the construction of an electrode electroencephalograph 39 having a plurality of types of electrodes 41 to 43. With reference to this figure, the relationship between the electrode type and an electroencephalogram signal (electroencephalogram channel) to be measured based on a potential difference between 1 set of electrodes will be described.

An electroencephalogram is measured in terms of potential difference between two electrodes which are worn on the head of a test subject. This potential difference corresponds to a potential change that has occurred in the brain of the test subject due to a neural activity. What defines an electroencephalogram waveform is representation of potential differences measured over a predetermined period.

The electroencephalograph 39 includes N measurement electrodes 41, a ground 42, and a reference electrode 43. Moreover, the electroencephalograph 39 includes differential amplifiers 40 corresponding to the N measurement electrodes 41.

Generally speaking, the measurement electrodes 41 are placed in sites at which encephalic activities for measurement are occurring. Moreover, the reference electrode 43 is placed at an ear periphery (earlobe or mastoid) or the like, where there is little influence of encephalic activities. Each differential amplifier 40 subjects a potential difference between a potential acquired by the reference electrode 43 and a potential acquired by the measurement electrode 41 corresponding to that differential amplifier 40 to differential amplification, and outputs the result. This output is the electroencephalogram signal at this site for measurement. By providing the differential amplifier 40, it becomes possible to amplify a very weak potential occurring in one's body. Also by providing the differential amplifier 40, it becomes possible to remove in-phase components of external origin, e.g., AC noise generated by a commercial device, when amplifying an electroencephalogram.

When amplifying a potential difference between two electrodes (the measurement electrode 41 and the reference electrode 43) for measurement, in addition to the two electrodes, a ground 42 input is separately used for the differential amplifier 40. The differential amplifier 40 amplifies a potential difference between the ground 42 and the measurement electrode 41 (i.e., the voltage of the measurement electrode 41 as measured on the basis of the ground) and a potential difference between the ground 42 and the reference electrode 43 (i.e., the voltage of the reference electrode 43 as measured on the basis of the ground). Furthermore, the differential amplifier takes a difference between the voltage of the measurement electrode 41 and the voltage of the reference electrode 43. As a result, any noise component that is contained alike at the measurement electrode 41 and at the reference electrode 43 can be removed. As described above, the potential difference between the amplified voltage of the measurement electrode 41 and the amplified voltage of the reference electrode 43 is measured as one electroencephalogram signal (or electroencephalogram data).

The method of measuring an amplified potential difference between two electrodes (the measurement electrode 41 and the reference electrode 43) is a mere example, and methods may be used. For example, a difference between a potential difference between the ground 42 and the measurement electrode 41 (i.e., the voltage of the measurement electrode 41 as measured on the basis of the ground) and a potential difference between the ground 42 and the reference electrode 43 (i.e., the voltage of the reference electrode 43 as measured on the basis of the ground) may be taken. Then this difference may be amplified and measured as one electroencephalogram signal.

This single electroencephalogram signal (or electroencephalogram data) obtained by the above method is referred to as an "electroencephalogram channel".

When performing a differential amplification for noise removal, each differential amplifier 40 outputs one electroencephalogram channel. In the example shown in FIG. 1, the number of electroencephalogram channels is N.

As described above, since one electroencephalogram is measured from the three electrodes of the measurement electrode 41, the ground 42, and the reference electrode 43, if even one of the three electrodes becomes insufficient, then the waveform of the electroencephalogram channel cannot be measured normally.

In a daily-life environment, any of the "measurement electrode", "ground", and "reference electrode" is liable to insufficient wearing. Hereinafter, manners in which insufficient wearing may occur will be described.

For example, portions (a) to (f) of FIG. 2 show an example of an eyeglass-type head-mount display (HMD) 50 in which dry electrodes for electroencephalogram measurement are incorporated, and their states of attachment. In the example of FIG. 2, measurement electrodes 41 are disposed at two positions above the eyes; a ground 42 is worn at the nose; and a reference electrode 43 is disposed behind an ear.

In a normal state (a), where the HMD 50 is normally worn, the electrodes are properly in contact with the skin. If the user moves in daily life, e.g., into a bending-over posture, the HMD 50 will be shifted forward, thus resulting in the state of (b). At this time, the measurement electrodes 41 above the eyes and the nose ground 42 will be detached from the user's skin, thus resulting in an insufficient state of electrode attachment.

Moreover, if the HMD 50 has been worn for a long time, the mass of the HMD may cause the HMD 50 to be shifted in the lower direction, thus resulting in the state of (c). At this time, the measurement electrodes 41 above the eyes will suffer from insufficient wearing.

Moreover, when the HMD 50 is touched for manipulation or adjustment, after an intense motion has been made, and so on, a state where the HMD 50 is lopsided may occur, thus resulting in the state of (d). As a result, the measurement electrodes 41 above the eyes and the ear reference electrode 41 may be detached from the user's skin, thus resulting in insufficient wearing. Furthermore, when bumping into something, etc., a state where the HMD 50 is shifted sideways may occur, thus resulting in the state of (e). In this state, it is expected that any one of the measurement electrode 41 above one eye or the nose ground 42, and the ear reference electrode 43 may become disengaged. Thus, due to motion or position shifting of the HMD 50, not only the measurement electrodes 41, but also the ground and reference electrodes are also liable to insufficient wearing.

In the state of (f), where the user's hair is caught between the reference electrode and the skin, the reference electrode 43 suffers from insufficient wearing.

Therefore, the inventors have conducted an experiment as follows.

Contemplating a situation where an electroencephalograph is incorporated into the aforementioned head-mount display (HMD), the inventors disposed the electrodes of an electroencephalograph within the range of the shape of an HMD. In the present specification, the "range of the shape" of a wearable device such as an HMD refers to a range that is occupied by a shape which is usually required of that device. For example, FIGS. 3A and 3B show positioning of electrodes which are provided within the range of the shape of an hair band 25 of an HMD. The electrodes are provided within a range of the head of the test subject that is covered by the hair band 25 as indicated by a broken line. The range of the HMD shape is also inclusive of the range that is covered by the hair band 25.

Specific examples of measurement electrode positions are as follows. First, a reference electrode 22 is disposed behind the right ear; a measurement electrode 1 (a measurement electrode 23*b* in FIG. 3A) is disposed above the left eye; and a measurement electrode 2 (a measurement electrode 23*a* in FIG. 3A) is disposed above the right eye. Then, a ground 21 is disposed at a position shown in the figure (this position corresponding to the FPz position according to the position notation of the International 10-20 system).

The reference electrode 22 is disposed behind an ear, which is far in distance from the brain (i.e., the generation source of an electroencephalogram), whereas the measurement electrodes 23 are disposed in two places above both eyes, which are close to the brain. This makes it possible to measure two electroencephalogram channels. Specifically, channel 1 (Ch1) is obtained with a combination of the ground 21, the reference electrode 22, and the measurement electrode 1, whereas channel 2 (Ch2) is obtained with a combination of the ground 21, the reference electrode 22, and the measurement electrode 2. As described above, a "channel" is an electroencephalogram signal (or electroencephalogram data) which is measured by a single differential amplifier (i.e., one measurement electrode, the reference electrode, and the ground being combined).

All of the electrodes used in the experiment, i.e., the measurement electrodes, the reference electrode, and the ground, are dry electrodes to be worn without paste. Silver-silver chloride active electrodes (i.e., electrodes which allow amplification to be performed not only inside the electroencephalograph but also inside the electrodes) are used as the measurement electrodes and the reference electrode. A silver-silver chloride disk electrode is used as the ground. The measurement electrodes, the reference electrode, and the ground were fixed in place with the hair band 25. Polymate AP-1124 (manufactured by DIGITEX LAB. CO., LTD) was used for the electroencephalogram measurements. A sampling frequency of 200 Hz and a time constant of 0.3 seconds were set. Under these conditions, the inventors conducted a measurement experiment for a test subject aged in the thirties.

The inventors have contemplated that the noise amount will fluctuate when any electrode becomes insufficient. Accordingly, changes in power at each frequency were observed, in a state where the electrodes were normally worn, and also in a state where an insufficiency in electrode attachment had occurred. Among others, attention was paid to the power of 60 Hz noise from commercial power, which is considered as the greatest external noise source, and to the power of the entire frequency band of the measured electroencephalogram, which is considered to reflect the entirety of the noise amount.

In electroencephalogram measurements, the amplitude voltage of an electroencephalogram signal to be measured is weak and in units of $\mu V$. On the other hand, the amplitude voltage of a noise component such as the 60 Hz noise from commercial power is in units of mV, which is greater than the amplitude voltage of an electroencephalogram signal. Moreover, a signal of brain origin is in the frequency band of 30 Hz or less. Thus, the 60 Hz noise from commercial power can be easily distinguished from a signal of brain origin. On the contrary, in electromyogram measurements, for example, the average potential of an electromyogram is generally said to be on the order of several $\mu V$ to several mV, with frequency components from several Hz to several 100 Hz; therefore, a potential of electromyogram origin is difficult to be distinguished from the 60 Hz noise from commercial power.

Therefore, the inventors have analyzed two kinds of parameters, i.e., noise amount and total frequency power.

The experiment determined an "amount of mixed AC noise", as an example of the noise amount. An amount of mixed AC noise is meant as an amount of commercial-power noise of an external device, e.g., a frequency power at 60 Hz.

As the total frequency power, an average value of power in the analyzable frequency band was determined. More specifically, 1 second of data was extracted from the measured electroencephalogram, and this was subjected to a fast Fourier transform (FFT) to determine a power value of each frequency; and a total frequency power was calculated as an average value of the power from 0 Hz to 100 Hz.

The reason for adopting "0 Hz to 100 Hz" is that, given the fact that electroencephalogram measurements were taken with a sampling frequency of 200 Hz in this experiment, the sampling theorem dictates that the available frequency band is up to 100 Hz.

In the present embodiment, the total frequency power is utilized as an index for checking for changes in the power of noises mixing in the available broad frequency band. The total frequency power is also utilized as an index for checking whether noises are mixed widely across a frequency band that is not associated with encephalic activities (i.e., a region of 30 Hz or above). Therefore, within the region of 30 Hz or above, by calculating a power average in a region accounting for a half or more of the available frequency band, a similar tendency to that of a power average value across the entire available frequency band (i.e., 0 to 100 Hz) will presumably be observed. Examples may be 30 Hz to 100 Hz, or 0 Hz to 60 Hz.

FIG. 4 shows results of the electroencephalogram analysis. FIG. 4 shows amounts of mixed AC noise and total frequency powers in channels 1 and 2 (Ch1, Ch2) for each of five different states. The five different states are: "all electrodes are properly worn (normal)", "only measurement electrode 1 is shifted (shifting measurement electrode 1)", "only measurement electrode 2 is shifted (shifting measurement electrode 2)", "the reference electrode is shifted (shifting reference electrode)", and "the ground is disengaged (disengaging the ground)". As used herein, "shifting" refers to a state where an electrode is moved to the right or left while the electrode remains attached on the skin.

From the values shown in a framing 501 in the rightmost column of FIG. 4, it can be seen that the amount of mixed AC noise increases only when the ground becomes insufficient (disengaging the ground), and that not much increase is seen in a normal state or when any other electrode becomes insufficient. On the other hand, when a measurement electrode becomes insufficient (shifting measurement electrode 1 or shifting measurement electrode 2), the total frequency power increases only in the channel that corresponds to the insufficient measurement electrode, as is indicated by the values in a framing 502 across two places in FIG. 4. From the values in a framing 503 in FIG. 4, it can be seen that both channel 1 and channel 2 increase when the reference electrode becomes insufficient (shifting reference electrode).

These experimental results have led to the finding that: the amount of mixed AC noise increases when the ground becomes insufficient; the total frequency power of a channel corresponding to the measurement electrode increases when a measurement electrode becomes insufficient; and the frequency powers of all channels increase when the reference electrode becomes insufficient.

Furthermore, in order to confirm whether the above finding dictates a phenomenon that occurs similarly in any other test subject, the inventors have conducted an electroencephalogram measurement experiment in 14 test subjects in their twenties. Given the same electroencephalograph, electrodes, and electrode positions as above, the experiment was conducted to measure amounts of mixed AC noise and total frequency powers in three states: (a) a state where all electrodes are correctly worn; (b) a state where the ground is insufficient (e.g., the ground is disengaged); and (c) a state where a measurement electrode is insufficient (e.g., the measurement electrode 1 is disengaged).

FIG. 5 shows an average value of amounts of mixed AC noise of all test subjects and an extent of variations among all test subjects in the three states of (a) normal, (b) disengaging the ground, and (c) disengaging a measurement electrode. Similarly to the results of disengaging the ground shown in a framing 501 in FIG. 4, in all test subjects, FIG. 5 indicates a tendency that the amount of mixed AC noise increases when (b) disengaging the ground, as compared to any other state.

FIG. 6 shows an average value of total frequency powers of all test subjects and an extent of variations among all test subjects in the three states of (a) normal state, (b) disengaging the ground state, and (c) disengaging a measurement electrode state. As shown in FIG. 6, similarly to the results in the framing 502 of FIG. 4, (c) a tendency found among all test subjects was that the total frequency power increases when a measurement electrode is disengaged, as compared to any other state.

This experiment was not directed to reference electrode insufficiencies. However, from the fact that a potential difference between a measurement electrode and a reference electrode is recorded as a potential waveform, and from the increased total frequency power associated with measurement electrode insufficiencies (shown in the framing 503 of FIG. 4 and FIG. 6), it is presumable that the total frequency powers of all channels will increase also when the reference electrode becomes insufficient, similarly to a measurement electrode insufficiency.

Moreover, in the case of hair pinching, even when the head (hair) is in contact with an electrode, there may actually be no electrical conduction because of the hair being an insulator. Therefore, similarly to electrode disengagement, hair pinching may presumably exert so much influence as to make electroencephalogram measurement impossible and increase the total frequency power.

It was learned from the above results that the above finding (i.e., the amount of mixed AC noise increases when the ground becomes insufficient; the total frequency power of a channel corresponding to the measurement electrode increases when a measurement electrode becomes insufficient; and the frequency powers of all channels increase when the reference electrode becomes insufficient) is not any specific tendency that is test-subject dependent.

Having obtained the above finding, the inventors have arrived at the concept that a ground insufficiency can be determined based on an increase in the amount of mixed AC noise, that a measurement electrode insufficiency can be determined based on an increase in the total frequency power in a specific channel, and that a reference electrode insufficiency can be determined based on an increase in the total frequency power of every channel.

(Method of Insufficiency Cause Estimation)

Next, a method of inferring an insufficiency cause by using a spatial pattern of insufficient electrodes which the inventors have accomplished will be described, while explaining how proper it is to switch remedies for different insufficiency causes.

First, as a premise, when measuring an electroencephalogram with a housing having electrodes incorporated therein, the housing shape constrains the freedom of electrode attachment. Therefore, when the housing shape is not proper relative to the head shape, "electrode disengagement" may occur, such that the electrode becomes lifted off the skin so as to be no longer in contact with the skin. Therefore, for stable electroencephalogram measurement, it is necessary to use a proper housing which is suited to the head shape of the user.

Generally speaking, depending on gender and age, the human head differs in size and shape. An adult head is usually larger than a child head, and a male head is often larger than a female head. Conventional electrode caps are available in the three sizes of Small, Middle, and Large. However, even given the same age and gender, user heads may vary in shape. For example, it is well known that head shapes tend to be more elliptical in westerners than in easterners. Apart from such differences, other individual differences are also known, e.g., shape irregularity as to right-left asymmetry of the head shape, the bulging and denting of the head shape, and so on. In the case of employing an electrode cap as in conventional practice, individual differences as to shape can be absorbed by the contraction and expansion properties of the cap. However, in the case where a housing with little electrode position freedom is employed in taking electroencephalogram measurements, it is not possible to accommodate every user with the three types of S/M/L alone. It is considered necessary to provide 10 or more types of housings at least differing in shape.

Examples of other techniques for alleviating disagreement between the head shape and the housing shape include: a method which involves providing a mechanism for absorbing the head shape differences, e.g., by way of springs provided within the housing; and a method which involves taking previous measurements of the head shape, and providing a housing with an optimum shape for each user. However, the former technique requires a special mechanism, which results in an increased mass of the housing and a poorer durability. In addition, springs or other like mechanisms can only work in a certain range, and it is difficult to deal with the head shape of every user. The latter technique would require a special apparatus for measuring the head shape.

The inventors have arrived at the concept that it is possible to take advantage of the low spatial freedom of electrode positioning in an electroencephalogram measurement which employs a housing, and identify an insufficiency cause by utilizing it. Specifically, from a spatial pattern of insufficient electrodes which are determined by the above-described method, a distinction can be made between insufficiencies due to electrode disengagement caused by disagreement between the housing shape and the head shape and insufficiencies caused by hair pinching.

Figure 7A:
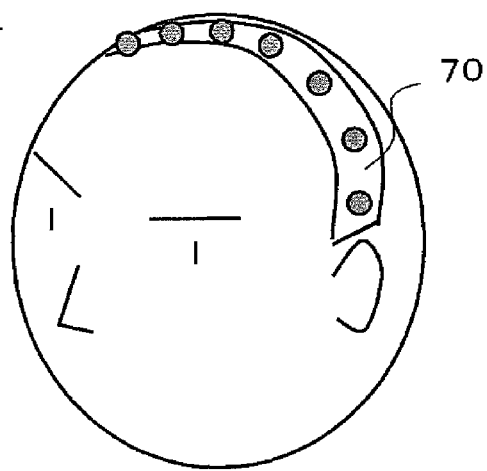
Figure 7B:
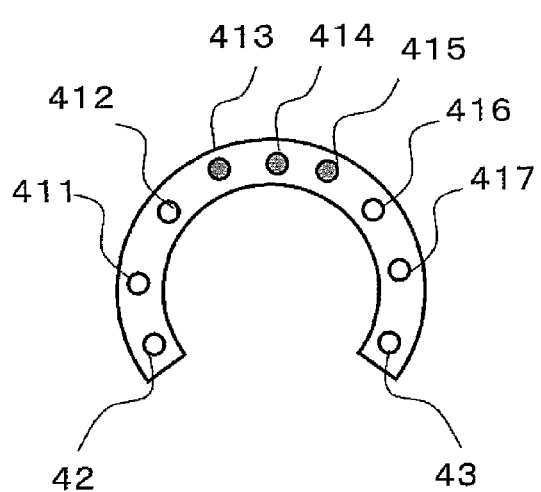

For example, FIG. 7A shows a headset-type housing in which dry electrodes for electroencephalogram measurement are incorporated, and examples of state of attachment thereof. FIG. 7B shows the positions of measurement electrodes 411 to 417. It is schematically illustrated that the measurement electrodes 411 to 417 are worn at positions ranging from above the right ear (measurement electrode 411; corresponding to T6 in the International 10-20 system), through a central portion (measurement electrode 414; corresponding to Cz in the International 10-20 system), to above the left ear (measurement electrode 417; corresponding to T7 in the International 10-20 system). The ground 42 and the reference electrode 43 are disposed so that the ground 42 is positioned above the right ear and the reference electrode 43 comes in contact with a position above the left ear when the housing 70 is worn by a user.

FIG. 7B illustrates an example where the result of insufficient electrode determination indicates that the measurement electrodes 413 to 415 are insufficient (electrode disengagement). Specifically, the measurement electrodes 413 to 415 are indicated with dark hatching, indicative that these electrodes are insufficient.

Figure 7C:
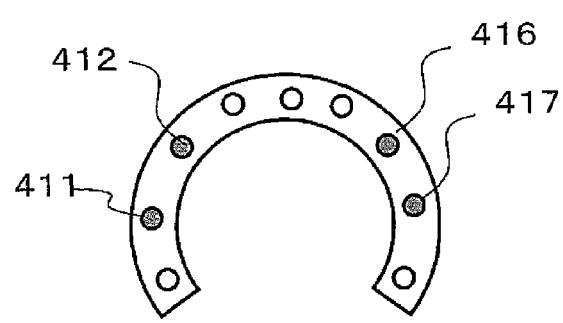

FIG. 7C illustrates an example where the result of insufficient electrode determination indicates that the measurement electrodes 411, 412, 416, and 417 are insufficient (electrode disengagement). A case as in FIG. 7B, where insufficiencies are detected at a plurality of sites in spatial proximity, and a case as shown in FIG. 7C, where insufficiencies are detected with a certain spatial pattern, both lead to the estimation that the cause of insufficiency is a disagreement between the head shape of the user the housing shape of the headset-type housing 70. Specifically, in FIG. 7B, for example, an electrode disengagement is occurring such that some electrodes are lifted around the measurement electrode 414, presumably because the user head is dented near the central portion relative to the housing shape. In FIG. 7C, for example, an electrode disengagement is occurring such that the measurement electrodes at the temples are lifted off, presumably because the user head has a small breadth relative to the housing shape.

Figure 7D:
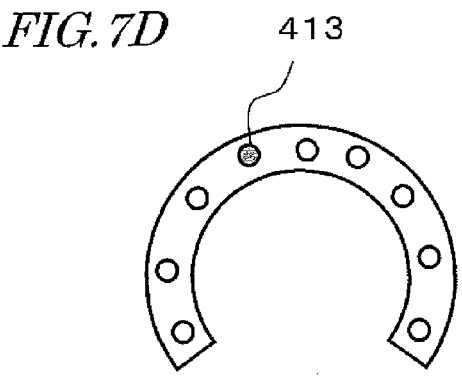

FIG. 7D illustrates an example where the result of insufficient electrode determination indicates that only the measurement electrode 413 is insufficient. When an insufficiency is detected in a single electrode as such, it is estimated that, although the housing shape agrees with the head shape, hair pinching has caused an insufficiency around that electrode alone. The estimation may be adapted to the distance between electrodes which are incorporated in the housing to judge that, in the case where the distance between electrodes is short, hair pinching exists also when a plurality of electrodes are insufficient.

The remedy for enabling stable electroencephalogram measurement may vary depending on the insufficiency cause. In the former instance (disagreeing head shape and housing shape; FIG. 7B and FIG. 7C), the housing shape needs to be changed. In the latter instance (hair pinching; FIG. 7D), however, the housing shape does not need to be changed, and the hair needs to be avoided at the measurement electrode 413.

For example, even if a remedy for hair pinching is adopted in the former instance, or housings with different shapes are worn in a hunt-down manner, the state of electrode attachment will remain the same or be deteriorated. On the other hand, in the latter instance, where the head shape already agrees with the housing shape, changing the housing shape will presumably deteriorate the state of electrode attachment.

Such hunt-down efforts are a burden to the user, and therefore a proper remedy for each insufficiency cause must be presented.

Similarly, also in the case of an HMD, for example, if a shape disagreement exists such that the head size of the user disagrees with the front width and/or temple length of the HMD, a specific pattern of electrode disengagements will occur in accordance with the type of shape disagreement. For example, if the front width of the HMD is shorter than the head breadth of the user, an electrode(s) near a mastoid(s) may become lifted, thus resulting in an electrode disengagement state. Conversely, if the front width of the HMD is longer, an electrode(s) near an outer canthus(s) may be lifted. Therefore, in the case of an HMD, too, it is possible to recommend a proper HMD in accordance with the spatial pattern of insufficient electrodes.

FIG. 8 shows a relationship between insufficiency causes and necessary remedies (outputs) for different results of insufficient electrode determination, as compiled by the inventors. Rows (a) to (d) in FIG. 8 correspond to FIGS. 7A to 7D, respectively. As shown in FIG. 8(a), when there are no insufficient electrodes, insufficiency cause estimation is not carried out, but the user may be notified that the electrode attachment is proper. Doing so will allow the user to begin electroencephalogram measurement without care. Although the present embodiment illustrates that a notification is output when the electrode attachment is proper, such notification is not essential. Instead, notification may be made only in the presence of an insufficient electrode(s).

As shown in FIG. 8(b), when a plurality of electrodes have become insufficient, it is estimated that disagreement between the head shape and the housing shape is the insufficiency cause, and that the disagreement in shape is occurring near the insufficient electrodes.

Then, an instruction to exchange the headset is given. In addition, a housing which is tighter around the insufficient electrodes is recommended. When insufficient electrodes occur in a certain spatial pattern as shown in FIG. 8(c), it is estimated that disagreement between the head shape and the housing shape is the insufficiency cause. Then, an instruction to exchange the headset is given, and a proper headset in accordance with the spatial pattern of insufficient electrodes is recommended. When a single insufficient electrode occurs at a haired site as shown in FIG. 8(d), it is estimated that hair pinching is the insufficiency cause. Then, the location of the insufficient electrode is indicated, and an instruction to avoid hair is output. Note that the determination as to whether a site is haired or not may be made in advance, based on information of sites which are expected to come in contact with the housing shape.

Thus, by estimating an insufficiency cause on the basis of the number and spatial pattern of insufficient electrodes known as a result of insufficient electrode determination, and switching the remedy (output) for each different estimated insufficiency cause, the troublesome hunt-down efforts for insufficiencies to be made by the user are reduced, and wearing of a housing having electrodes incorporated therein is made easy.

Hereinafter, embodiments of an electrode attachment state determination system according to the present disclosure, which are made based on these concepts, will be described with reference to the drawings.

As exemplary embodiments of the present disclosure, the inventors will illustrate an electroencephalogram measurement system (hereinafter referred to as a "simplified electroencephalogram measurement system") in which a housing having electrodes incorporated therein is worn by a user for measuring an electroencephalogram of the user, and feedback of a state of electrode attachment is provided. It is assumed that dry electrodes are incorporated in the housing of e.g. an HMD or a headset in the simplified electroencephalogram measurement system. Then, the simplified electroencephalogram measurement system determines a state of electrode attachment, estimates an insufficiency cause from the number and spatial pattern of insufficient electrodes, and feeds it back to the user as the state of electrode attachment. In addition to the state of electrode attachment, an instruction of a proper remedy is given for each insufficiency cause. Note that the simplified electroencephalogram measurement system can be used in an electroencephalogram interface system which determines a user state or intent from a characteristic signal of the measured electroencephalogram and feeds back a result of determination, for example.

(Embodiment 1)

FIG. 9 shows the functional block construction of a simplified electroencephalogram measurement system 20 according to the present embodiment. FIG. 10 shows an exemplary device shape in the case where the simplified electroencephalogram measurement system 20 is embodied as a headset. FIG. 11 shows an exemplary hardware construction of the simplified electroencephalogram measurement system 20. Among the constituent elements shown in each figure, like constituent elements are denoted by like reference numerals.

In the present specification, the simplified electroencephalogram measurement system 20 will be described on the basis of a headset shape shown in FIG. 10.

As shown in FIG. 9, the simplified electroencephalogram measurement system 20 includes an electroencephalogram measurement/processing section 18 and an electrode state determination processing section 19. FIG. 9 illustrates a user 10 for ease of understanding.

The electroencephalogram measurement/processing section 18 includes an electroencephalogram measurement section 11 and an output section 12. The electrode state determination processing section 19 includes a frequency analysis section 13, an insufficient electrode determination section 14, an insufficiency cause estimation section 15, and an electrode position storing section 16. Hereinafter, the respective constituent elements will be described.

The electroencephalogram measurement section 11 of the electroencephalogram measurement/processing section 18 includes a ground 21, a reference electrode 22, seven measurement electrodes 23*a* to 23*g*, and an electroencephalogram measurement circuit 24 shown in FIG. 10. The ground 21 is disposed so that contact occurs above the right ear; the reference electrode 22 is disposed so that contact occurs above the left ear; the seven measurement electrodes 23*a* to 23*g* are each disposed on the inside of the headset; and the electroencephalogram measurement circuit 24 is disposed near the ground 21, within the headset. These electrodes are disposed so that they come into contact with the skin of the user 10 when the headset is worn.

The output section 12, which may be a display or the like, may be provided separately from the simplified electroencephalogram measurement system 20 and wirelessly connected thereto. Alternatively, the headset may have a display provided thereon. Feedback is realized in the form of an operation such as providing an image output to the display. Note that the output section 12 may provide an audio presentation or the like instead.

The frequency analysis section 13 of the electrode state determination processing section 19 is disposed inside the headset, and analyzes the frequency of an electroencephalogram which is measured by the electroencephalogram measurement section 11.

From the value of frequency analysis, the insufficient electrode determination section 14 determines an electrode that has become insufficient.

Based on the number and spatial pattern of insufficient electrodes having been determined by the insufficient electrode determination section 14, the insufficiency cause estimation section 15 estimates an insufficiency cause, and notifies the user 10 of the state of electrode attachment via the output section 12. The information concerning the positions of the insufficient electrodes is acquired by referring to insufficiency patterns that are retained in the electrode position storing section 16. Specifically, an "insufficiency pattern" is a pattern in which the number of insufficient electrodes, the position(s) at which the insufficient electrode(s) is in contact with the user, and a cause for the insufficient state of attachment are associated.

The electrode position storing section 16 retains information of the electrode positions of the ground, the measurement electrodes, and the reference electrode.

The information of the electrode positions may be retained in an orthogonal coordinate system (x, y, z), or in a polar coordinate system (r, θ, φ), for example.

Note that the functional blocks and electrode positions in FIG. 10 are exemplary, and the positions of the functional blocks, the positions of the electrodes, and the number thereof are not limited thereto.

Next, the hardware construction of the simplified electroencephalogram measurement system 20 will be described with reference to FIG. 11.

The ground 21, the reference electrode 22, the plurality of measurement electrodes 23, and the electroencephalogram measurement circuit 24 constitute the electroencephalogram measurement section 11 according to the present embodiment. The ground 21, the reference electrode 22, and the plurality of measurement electrodes 23 are connected to the electroencephalogram measurement circuit 24. The electroencephalogram measurement circuit 24 is connected to a bus 100 for exchange of electroencephalogram signals with other constituent elements.

Next, a CPU 131, a RAM 132, and a ROM 133 constitute the frequency analysis section 13 according to the present embodiment. The CPU 131 reads a computer program 134 which is stored in the ROM 133 onto the RAM 132, where the computer program 134 is laid out and executed. Based on the computer program 134, the frequency analysis section 13 of the present embodiment realizes a frequency analysis process for the electroencephalogram waveform. The CPU 131, the RAM 132, and the ROM 133 are connected to the bus 100 for sending data representing an analysis result to the insufficient electrode determination section 14.

A CPU 141, a RAM 142, and a ROM 143 constitute the insufficient electrode determination section 14 according to the present embodiment. The CPU 141 reads a computer program 144 which is stored in the ROM 143 onto the RAM 142, where the computer program 144 is laid out and executed. Based on the computer program 144, the insufficient electrode determination section 14 of the present embodiment realizes an insufficient electrode determination process described later. The CPU 141, the RAM 142, and the ROM 143 are connected to the bus 100, for exchange of control signals and data with the output section 12.

A CPU 151, a RAM 152, and a ROM 153 constitute the insufficiency cause estimation section 15 according to the present embodiment. The CPU 151 reads a computer program 154 which is stored in the ROM 153 onto the RAM 152, where the computer program 154 is laid out and executed. Based on the computer program 154, the insufficiency cause estimation section 15 of the present embodiment realizes an insufficiency cause estimation process described below. The CPU 151, the RAM 152, and the ROM 153 are connected to the bus 100 for exchange of control signals and data with the output section 12.

The output section 12 includes an image processing circuit 121 and a screen 122. In accordance with control signals and data from the CPUs 121 and 151, the image processing circuit 121 outputs information of the state of electrode attachment to the user 10. The output section 12 may also have a function of presenting necessary information on the headset.

Each of the aforementioned computer programs 134, 144, and 154 may be distributed on the market in the form of a product recorded on a semiconductor memory medium or a storage medium such as a CD-ROM, or transmitted through telecommunication lines such as the Internet.

Note that the frequency analysis section 13, the insufficient electrode determination section 14, and the insufficiency cause estimation section 15 may each be implemented as a piece of hardware (e.g., a DSP) consisting of semiconductor circuitry having the computer program(s) incorporated therein, or as a semiconductor device which performs calculations by its own circuitry, not via a CPU. Although the frequency analysis section 13, the insufficient electrode determination section 14, and the insufficiency cause estimation section 15 are illustrated as functional blocks having separate CPUs, RAMs, and ROMs, their functions may similarly be realized by a shared CPU, RAM, and ROM.

Next, an outline of the simplified electroencephalogram measurement system 20 of the present disclosure will be described, and after briefly discussing the processing thereof, a method of determining insufficiencies concerning the state of electrode and a method of insufficiency cause estimation will be described in detail.

The simplified electroencephalogram measurement system 20 analyzes the measured electroencephalogram, and identifies whether any insufficiency has occurred in the state of electrode attachment or not. When any insufficient electrode exists, the simplified electroencephalogram measurement system 20 estimates an insufficiency cause and notifies it to the user. When there is no insufficiency, the simplified electroencephalogram measurement system 20 notifies the user that the state of electrode attachment is good.

FIG. 12 shows a flowchart of an overall processing by the simplified electroencephalogram measurement system 20. Hereinafter, an operation will be described in accordance with the flowchart of the simplified electroencephalogram measurement system 20 in FIG. 12.

At step S1101, the electroencephalogram measurement section 11 measures an electroencephalogram of the user 10. The electroencephalogram measurement is taken by the electroencephalogram measurement circuit 24 with respect to each set (channel), where one set is defined by three types of electrodes shown in FIG. 10, i.e., the ground 21, the reference electrode 22, and a measurement electrode 23 corresponding to the measurement channel (i.e., one of the measurement electrodes 23a to 23g). Note that the ground 21 and the reference electrode 22 are commonly shared among the respective sets.

On the basis of the potential of the ground 21, the electroencephalogram measurement circuit 24 performs a differential amplification. Specifically, the electroencephalogram measurement circuit 24 amplifies the potential of the reference electrode 22 and the potential of the measurement electrode 23 on the basis of the potential of the ground 21, and takes a difference of the amplified potential of the reference electrode 22 from the amplified potential of the measurement electrode 23. As a result, an electroencephalogram potential of the measurement electrode 23 based on the reference electrode 22 can be measured. This differential amplification is to be used for amplifying weak signals, and also used in electroencephalogram measurements. The electroencephalogram potential measured in the above manner is sent to the frequency analysis section 13 of the electrode state determination processing section 19 as one channel of electroencephalogram data.

At step S1102, the frequency analysis section 13 performs a frequency analysis process. FIG. 13 shows an example of an electroencephalogram signal waveform to be processed by the frequency analysis section 13. The frequency analysis section 13 receives an electroencephalogram signal 301 which has been measured by the electroencephalogram measurement section 11, and extracts an electroencephalogram waveform 302 from a zone for determination. The zone to be extracted here is prescribed to be 1 second, for example. Next, the frequency analysis section 13 subjects the extracted electroencephalogram signal 302 to a frequency analysis based on fast Fourier transform (FFT), for example, and calculates power values 303 of respective frequencies. The power values 303 of respective frequencies correspond to Fourier coefficient values that are obtained from the fast Fourier transform (FFT).

After the power value calculation, the frequency analysis section 13 outputs the result of frequency analysis to the insufficient electrode determination section 14. After outputting the frequency analysis result, the frequency analysis section 13 waits until 1 second of electroencephalogram is measured, and after the lapse of 1 second, again executes a frequency analysis. If no process timing for the frequency analysis section 13 arrives during the zone for analysis or longer, the electroencephalogram data from 1 second immediately before the process timing is subjected to a frequency analysis.

At step S1103, the insufficient electrode determination section 14 determines whether each of the electrodes used for electroencephalogram measurement is suffering from insufficient wearing or not. From the frequency analysis result from the frequency analysis section 13, the insufficient electrode determination section 14 extracts analysis parameters which are necessary for determining the state of electrode attachment, i.e., noise amount and total frequency power. Then, through a comparison between each analysis parameter and a predetermined threshold value, the insufficient electrode determination section 14 determines whether each of the ground, reference electrode, and measurement electrodes is suffering from insufficiency in the state of electrode attachment. If any such insufficiency has occurred, the insufficient electrode determination section 14 performs a process of identifying which of the ground, reference electrode, and measurement electrodes has become insufficient. The specific determination method will be described in detail later.

If any insufficient electrode is detected, control proceeds to step S1104; if no insufficient electrode is detected, control proceeds to step S1105.

At step S1104, the insufficiency cause estimation section 15 receives number information of the insufficient electrode(s) detected by the insufficient electrode determination section 14, and refers to the electrode position storing section 16 to identify the spatial position of insufficient electrode(s). Then, from the number of insufficient electrodes and the spatial pattern of insufficient electrodes, an insufficiency cause is estimated. The method of insufficiency cause estimation will be described later.

At step S1105, when receiving information from the insufficient electrode determination section 14 that no insufficiency is detected, the output section 12 notifies the user 10 that the electrode attachment is proper. Or, when receiving information of an estimated insufficiency cause from the insufficiency cause estimation section 15, the output section 12 notifies the user 10 of the estimated insufficiency cause. FIGS. 19A to 19C show examples of states of attachment of electrodes which may be output from the output section 12. FIG. 19A shows an exemplary output in the case where there is no insufficient electrode, such that the housing having electrodes incorporated therein is properly worn. FIG. 19B shows an exemplary output in the case where a plurality of insufficient electrodes exist and it is estimated from their spatial pattern that the insufficiency cause is disagreement between the head shape and the housing shape. FIG. 19C shows an exemplary output in the case where hair pinching is estimated to be the insufficiency cause.

Moreover, when no disagreement is estimated between the head shape and the housing shape, it might be possible for the electroencephalograph to be normally worn, once the user wears the electroencephalograph again. Therefore, instead of FIG. 19C, an output such as "Please wear it again" may be made to urge re-wearing. When it has been estimated that hair is pinched under an electrode(s) in the central portion as shown in FIG. 19C, an output may be made to say "Please wear it again, with attention to electrodes in the central portion".

Note that the output method to the user is not limited to the above, but any other method may be adopted. For example, an LED lamp may be provided outside the screen, and elimination of insufficiencies in the state of attachment may be notified by utilizing the color of the LED lamp. The LED lamp may be activated in green in the normal state, or in red when insufficiencies have occurred, and again in green when the insufficiencies have been eliminated. Alternatively, an audio saying "Restored" or the like may be generated and used for notification. Furthermore, any notifying method other than visual is also encompassed by the present disclosure, e.g., allowing an alarm sound that is output as a notice while there is any insufficiency to be stopped upon restoration from the insufficiency.

Note that the person who is notified of insufficiencies may not be the same user that is wearing the HMD.

Through such processes, the user can be notified as to whether the state of electrode attachment is good or not, or when any insufficiency has occurred, notified of the cause of insufficiency.

(Details of Insufficient Electrode Determination Process)

Next, the process of determining an insufficient electrode which is performed by the insufficient electrode determination section 14 at step S1103 in FIG. 12 will be described.

FIG. 14 shows a flowchart of processing by the insufficient electrode determination section 14 which is performed at step S1103 (FIG. 12). Hereinafter, the details of the process performed at step S1103 will be described.

At step S1201, the insufficient electrode determination section 14 acquires a frequency analysis result which is output from the frequency analysis section 13. As used herein, the frequency analysis result may be data of the frequency power value of each frequency band. For example, in the case of recording the electroencephalogram with a sampling period of 200 Hz, it will be a result of a frequency analysis (FFT) with half a period thereof, i.e., from 0 to 100 Hz.

At step S1202, from the frequency analysis result of each electroencephalogram channel (Ch), the insufficient electrode determination section 14 calculates a characteristic noise frequency power. As used herein, a characteristic noise frequency is a frequency of noises occurring from an external device or the like in an environment in which the electroencephalogram is being measured. These noises are contained in the electroencephalogram signal at this frequency. For example, in an environment which is surrounded by electric devices, AC noise from the power source may be a characteristic noise. Inside an automobile, for example, a similar characteristic noise may be the pulse waves generated from the engine. The frequency of pulse waves generated from the engine will be in proportion to the engine revolutions. Therefore, by acquiring information representing the engine revolutions from a tachometer, a computer, or the like of the automobile, the insufficient electrode determination section 14 will be able to identify the frequency of the pulse waves.

The aforementioned AC noise frequency or engine pulse wave noise frequency is calculated from the frequency analysis result of each channel. This calculated frequency is defined as a "characteristic noise frequency".

The embodiment contemplates indoor use of the simplified electroencephalogram measurement system, and assumes that the characteristic noise is an AC noise. The AC noise band is 60 Hz in the kansai (west) region, and 50 Hz in the kanto (east) region, of Japan. Since the environment where the aforementioned experiment was conducted was in the kansai region, it is assumed that the characteristic noise frequency is 60 Hz, and the characteristic noise frequency power will read as the "amount of mixed AC noise" in the following description. Note that, the AC noise bands in other countries are 60 Hz for the United States of America, and 50 Hz for European countries and China. Based on the 60 Hz scenario described below, those skilled in the art should be able to similarly conduct an experiment and use the simplified electroencephalogram measurement system in any 50 Hz locality by considering the frequency difference.

At step S1203, from the frequency analysis result of each electroencephalogram channel, the insufficient electrode determination section 14 calculates a total frequency power. The total frequency power is calculated as an average value of the powers of the frequency analysis results (i.e., an average of frequency powers from 0 to 100 Hz).

In the processes of step S1204 and after, based on the values of the noise amount and total frequency power, the insufficient electrode determination section 14 determines which of the ground 21, the reference electrode 22, and the measurement electrode 23 has become insufficient. The flow of determination is in the following order: insufficiency determination for the ground 21 (step S1205), insufficiency determination for the measurement electrode 23 (steps S1205, S1206, and S1208), and then insufficiency determination for the reference electrode 22 (step S1209). These determination methods will be specifically described below.

First, the insufficient grounding determination performed by the insufficient electrode determination section 14 (step S1204) will be described. By referring to the amount of mixed AC noise calculated at step S1202, the insufficient electrode determination section 14 determines whether the ground 21 has become insufficient or not.

FIG. 15 presents, with respect to the results of the aforementioned experiment conducted by the inventors (FIG. 4) as an example, an exemplary graph representation of a frequency analysis result in the case where the ground 21 is normally worn (normal state) and a frequency analysis result in the case where the ground is disengaged (insufficient grounding). In the graph, the horizontal axis represents frequency (unit: Hz), and the vertical axis represents frequency power (unit: $\mu V^2$). This is a graph representation of the relationship between frequency powers at 60 Hz in a normal state and under insufficient grounding, obtained by utilizing the amount of mixed AC noise of Ch1 in FIG. 4. According to FIG. 16, as compared to 82.3 $\mu V^2$ in the normal state, the value under insufficient grounding is 35502.3 $\mu V^2$, which is very different.

Therefore, a threshold value for ground insufficiency determination is set in the insufficient electrode determination section 14 in advance, and when the amount of mixed AC noise exceeds the threshold value, the insufficient electrode determination section 14 determines that the ground 21 has become insufficient. As the "threshold value", it is desirable to set an intermediate value between the normal state and insufficient grounding. However, by taking into consideration the discrepancy between the value in the normal state and the value under insufficient grounding, in the present embodiment, a logarithm of the amount of mixed AC noise in the normal state and a logarithm of the amount of mixed AC noise under insufficient grounding were averaged, and a frequency power that corresponds to this average value, i.e., 1700 $\mu V^2$, was set.

Another method of threshold value setting may be a method of, based only on the value in the normal state, defining an abnormal state by a value which is 10 times as large as that in the normal state (insufficient grounding state), i.e., 823 $\mu V^2$, for example. Through a comparison between this threshold value and the amount of mixed AC noise, in the experimental example of FIG. 4, the normal state will be determined as "no insufficient grounding", and control proceeds to step S1205. Moreover, the state of "disengaging the ground" will be determined as "insufficient grounding", and control proceeds to step S1210 of outputting a notice of insufficiency to the output section 12.

FIG. 19A shows an example of a notice of insufficiency when an insufficient grounding determination is made. As shown in FIG. 19A, an alarm indicating that the ground is disengaged is displayed on a screen 122. Alternatively, as shown in FIG. 19B, an image and explanation may be displayed on a screen 122 which indicates an electrode position where abnormal wearing is occurring.

Referring back to FIG. 14, the insufficiency determination process for the measurement electrodes 23 performed by the insufficient electrode determination section 14 (steps S1205, S1206, and S1208) will be described.

At step S1205, by utilizing the characteristics of the aforementioned experiment conducted by the inventors, the insufficient electrode determination section 14 compares the value of the total frequency power of any one channel that has been measured, against the threshold value for determining electrode insufficiency. If the total frequency power of an electroencephalogram channel for determination exceeds the threshold value, the insufficient electrode determination section 14 determines that the measurement electrode of the determined channel number may have become insufficient, and records the channel number in an insufficiency list at step S1208. FIG. 16 shows an exemplary insufficiency list in which the channel numbers which have become insufficient are recorded.

According to the above experimental results, the threshold value was set to 36 $\mu V^2$, which is an intermediate value between the greater of the total frequency power values in the normal state (i.e., 5.2 $\mu V^2$) and the smallest of the total frequency power values which have increased with an electrode insufficiency (i.e., 67.1 $\mu V^2$).

In the experimental example of FIG. 4, when measurement electrode 1 is shifted, Ch1 whose total frequency power exceeds 36 $\mu V^2$, is detected to be insufficient, and added to the insufficiency list. Another method of threshold value setting may be setting a threshold value for each channel, and based only on the value in the normal state, defining an abnormal state (measurement electrode insufficiency state) by a value which is twice as large as that of the normal state (e.g., 10.4 $\mu V^2$ for Ch1 and 5.6 $\mu V^2$ for Ch2).

Regarding the frequency power values at the time of insufficiencies, the same values as those obtained through the above experimental analysis will not always occur at the time of electrode insufficiencies; rather, they will presumably vary depending on the degree and extent of electrode shifting and on the skin state. However, the tendency will remain that the total frequency power increases at the time of insufficiencies over that in the normal state. Therefore, by taking into consideration the fluctuations in the total frequency power values at the time of insufficiencies, the threshold value for distinction may be set lower than the aforementioned value (e.g., 20 $\mu V^2$).

At step S1206, the insufficient electrode determination section 14 determines whether any electroencephalogram channel exists that has not been subjected to the comparison process of step S1205. If there is any, control returns to step S1205, and the electroencephalogram channel is subjected to the comparison process of step S1205.

If the comparison process of step S1205 has been completed from all electroencephalogram channels, the process proceeds to step S1207. At step S1207, the insufficient electrode determination section 14 confirms the contents of the insufficiency list, and confirms the channel numbers described in the insufficiency list. If the insufficiency list contains no description and is empty, the insufficient electrode determination section 14 determines that there are no insufficient electrodes, and makes a "no insufficient electrodes" determination at step S1213.

If the insufficiency list is not empty, then at step S1209, the insufficient electrode determination section 14 determines whether all of the electroencephalogram channels that are currently under measurement are in the insufficiency list or not. If all of the channels are in the insufficiency list, it is considered that the reference electrode 22 has become insufficient. Therefore, the insufficient electrode determination section 14 determines at step S1211 that the reference electrode is insufficient.

If step S1209 finds that the insufficiency list does not match all of the channel numbers, it is presumable that an individual measurement electrode(s) has become insufficient. At step S1212, the insufficient electrode determination section 14 determines that the measurement electrode(s) corresponding to the Ch number(s) in the insufficiency list is insufficient.

Now, the flow of the determination process shown in FIG. 14 will be discussed with reference to the results shown in FIG. 4 of the normal state, measurement electrode 1 being insufficient, measurement electrode 2 being insufficient, and the reference electrode being insufficient.

In the normal state, the insufficient electrode determination section 14 will not add Ch1 and Ch2 to the insufficiency list through the processes of steps S1205 to S1207 in FIG. 14. The reason is that the total frequency powers of Ch1 and Ch2, i.e., 5.2 $\mu V^2$ and 2.8 $\mu V^2$, are both under the threshold value of 36 $\mu V^2$. Then, the insufficient electrode determination section 14 will confirm at step S1207 that the insufficiency list is empty, thus making a "no insufficient electrodes" determination.

When measurement electrode 1 is shifted, the total frequency power of Ch1, i.e., 93.7 $\mu V^2$, exceeds the threshold value of 36 $\mu V^2$. Therefore, through the processes of step S1205 and step S1208 in FIG. 14, the insufficient electrode determination section 14 will add channel numbers including measurement electrode 1 to the insufficiency list. Since the insufficient electrode determination section 14 determines that only Ch1 is insufficient at step S1209, measurement electrode 1 is determined as an insufficient electrode.

When the reference electrode is shifted, the total frequency powers of Ch1 and Ch2, i.e., 357.6 $\mu V^2$ and 194.6 $\mu V^2$, are both below the threshold value of 36 $\mu V^2$. Therefore, through the processes of step S1205 and step S1208 in FIG. 14, the insufficient electrode determination section 14 will add Ch1 and Ch2 to the insufficiency list. At step S1209, determining that all channels are suffering from insufficiencies, the insufficient electrode determination section 14 determines the reference electrode to be the insufficient electrode.

Through the above processes, it is possible to identify whether an electrode which has become insufficient is a measurement electrode, the reference electrode, or the ground. Furthermore, it is possible to identify which one of a plurality of measurement electrodes has become insufficient.

(Details of Insufficiency Cause Estimation Process)

Next, an insufficiency cause estimation process which is performed by the insufficiency cause estimation section 15 at step S1104 in FIG. 12 based on the number and spatial pattern of insufficient electrodes will be described.

FIG. 17 shows a flowchart of processes which are performed by the insufficiency cause estimation section 15 at step S1104 (FIG. 12). The processes performed at step S1104 will be described in detail below.

At step S1501, from the insufficient electrode determination section 14, the insufficiency cause estimation section 15 receives a list of channel numbers of insufficient electrodes as shown in FIG. 16. Then, the number of insufficient electrodes is determined, and by referring to the electrode position storing section 16, three-dimensional electrode positions corresponding to the channel numbers of the insufficient electrodes are identified. For example, if the electrode positions for each channel are retained in an orthogonal coordinate system in the electrode position storing section 16, x, y, z values are received as the positions of the insufficient electrodes.

At step S1502, the insufficiency cause estimation section 15 determines whether the number of insufficient electrodes determined at step S1501 is singular or plural. If Yes at step S1502 (i.e., there is a plurality of insufficient electrodes), the process proceeds to step S1503; if No at step S1502 (i.e., there is one insufficient electrode), the process proceeds to step S1506.

At step S1503, the insufficiency cause estimation section 15 compares insufficiency patterns that are retained in a storage section of the insufficiency cause estimation section 15 against the spatial pattern of insufficient electrodes which has been identified at step S1501, and calculates a degree of matching therebetween, which may be a correlation coefficient, for example.

FIG. 18 shows exemplary insufficiency patterns retained in the insufficiency cause estimation section 15. FIG. 18 illustrates an example where standardized orthogonal coordinate system values are retained as electrode positions, and a plurality of insufficiency patterns are retained for different types of shape disagreement between the head and the housing. For each type of shape disagreement, "X" symbols indicate examples of electrode positions at which insufficiencies are likely to occur. For instance, as indicated in the "DENT IN CENTRAL PORTION" column, an insufficiency pattern with X symbols near the central portion is retained for the case where the user head is dented in the central portion relative to the housing shape. On the other hand, the aforementioned case of reference electrode disengagement would correspond to an insufficiency pattern with X symbols given for all electrodes, since the total frequency power will increase at every electrode. Note that the insufficiency patterns may be generated on the basis of a typical head shape pattern of an envisaged user group, and updated as necessary.

FIG. 17 is referred to again. Step S1504 represents a branching at the insufficiency cause estimation section 15, which occurs in accordance with the degree of matching from step S1503. When the degree of matching is higher than a predetermined threshold value, the process proceeds to step S1505; if it is lower, the process proceeds to step S1506. The degree of matching may be determined as a correlation coefficient between each insufficiency pattern and the detected insufficient electrodes, or determined by dividing the number of electrodes that match each insufficiency pattern by the total number of electrodes, for example. In the case where the degree of matching is defined as a correlation coefficient, 0.7 may be set as the predetermined threshold value, for example.

At step S1505, the insufficiency cause estimation section 15 estimates the insufficiency cause to be disagreement between the head shape and the housing shape.

At step S1506, the insufficiency cause estimation section 15 estimates the insufficiency cause to be hair pinching.

Through the above processes, based on the number and spatial pattern of insufficient electrodes, a distinction as to the insufficiency cause can be made between: disagreement between the head shape and the housing shape; and hair pinching.

The determination of step S1502 is made based on whether the number of insufficient electrodes determined by the insufficiency cause estimation section 15 at step S1501 is plural or not. Alternatively, this determination may be made based on whether a greater number of insufficient electrodes than a predetermined threshold value exist or not. The predetermined threshold value for distinction between hair pinching and disagreement between the head shape and the housing shape can be set based on the distance between electrodes. For example, a greater threshold value may be set as the distance between relevant electrodes decreases.

Another type of insufficiency pattern may indicate there being a greater number of insufficient electrodes than a predetermined threshold value, the insufficiency electrodes adjoining one another at contiguous electrode positions, for example.

The determination of step 1504 is based on a degree of matching, rather than on whether the electrodes having been determined as insufficient match an insufficiency pattern or not. Use of a degree of matching makes it possible to determine hair pinching occurring in a plurality of sites, and also determine an instance where both of hair pinching and disagreement between the head shape and the housing shape are occurring. For example, an envisaged user group may be asked in advance to actually use an electroencephalograph which is constructed in a certain housing, and a threshold value specific to that housing may be determined such that a smaller predetermined threshold value is prescribed as hair pinching occurs more frequently.

By outputting this result of insufficiency cause estimation via the output section 12, when the electrode attachment is not proper and there exists an insufficient electrode(s), the user is allowed to immediately confirm the insufficiency cause thereof.

With the simplified electroencephalogram measurement system 20 of the present embodiment, when a housing having electrodes incorporated therein is worn for electroencephalogram measurement, it can be determined whether the state of electrode attachment is sufficient or not. Moreover, when there is any insufficiency in electrode attachment, an insufficiency cause can be estimated from the number and spatial pattern of insufficient electrodes, and then notified to the user. This makes it possible to reduce hunt-down efforts for insufficiencies of electrode attachment, and realize stable electroencephalogram measurement with ease.

(Embodiment 2)

By using the simplified electroencephalogram measurement system of Embodiment 1, the user 10 becomes able to immediately confirm whether the state of electrode attachment is sufficient or not when wearing a housing having electrodes incorporated therein for electroencephalogram measurement. When there is any insufficiency in electrode attachment, it is also possible to know whether the insufficiency cause is disagreement of the housing shape or hair pinching. This makes it unnecessary to make hunt-down efforts for insufficiency in electrode attachment, and realize stable electroencephalogram measurement with ease.

However, when the insufficiency cause is hair pinching, as the user 10 tries to remove the hair that is caught between the insufficient electrode(s) and the skin, electrodes that are near the insufficient electrode(s) may possibly suffer from new insufficiencies, e.g., electrode shifting, even though they were never insufficient before. This causes a problem in that the overall electrode position correction may take time.

Therefore, in the present embodiment, an insufficiency restoration determination section is newly provided to ensure that electrode insufficiencies will not be detected until restoration of the insufficient electrodes is complete, thus reducing the burden of the user 10 during insufficiency correction.

First, a method of determining insufficient electrode restoration will be described below.

In addition to the above-described experiment, the inventors have conducted an experiment to look for characteristic features of the electroencephalogram that distinguish a state where an electrode insufficiency has not been eliminated from a state where the electrode has been restored. As a result, they have found that, by detecting a characteristic feature which appears when an insufficient electrode is restored, it is possible to perform an electrode restoration determination process.

Hereinafter, details of this experiment and the novel findings obtained from the experimental results will be described, followed by a description of the details of a restoration determination process for insufficient electrodes that utilizes the findings.

In this experiment, similarly to the previous experiment, electrodes were worn by a test subject aged in the thirties at positions shown in FIGS. 3A and 3B: a reference electrode 21 behind the right ear; a measurement electrode 23a above the right eye; a measurement electrode 23b above the left eye; and a ground 21 at FPz according to the position notation of the International 10-20 system. Silver-silver chloride active electrodes were used as the measurement electrodes and as the reference electrode, whereas a silver-silver chloride disk electrode was used as the ground, each without using paste; and these were fixed with a hair band 25. Polymate AP-1124 (manufactured by DIGITEX LAB, CO., LTD) was used as an electroencephalograph. The measurements were taken with a sampling frequency of 200 Hz and a time constant of 0.3 seconds.

The experiment was conducted under the assumption that the measurement electrodes or the ground may be an insufficient electrode(s). It was assumed that a characteristic feature similar to that associated with the measurement electrodes will also appear for the reference electrode.

The assumed insufficiency state was "electrode disengagement", and a comparison was made between an electroencephalogram waveform of the case where an electrode was left disengaged and an electroencephalogram waveform of the case where an electrode was once disengaged and then immediately corrected and restored to the normal state. Specifically, the experiment was conducted in four states: "(a) the measurement electrode 23b is left disengaged"; "(b) the measurement electrode 23b is temporarily disengaged and then restored to the correct state"; "(c) the ground 21 is left disengaged"; and "(d) the ground 21 is temporarily disengaged and then restored to the correct state". The inventors measures electroencephalograms in the respective states, and conducted a comparison in the electroencephalogram waveforms between (a) and (b), which involves comparison between the measurement electrodes 23, and a comparison in the amounts of mixed AC noise between (c) and (d), which involves comparison concerning the ground 21.

FIGS. 20(a) to (d) respectively show results of the experiment. In each graph, the horizontal axis represents time (unit: second). In (a) and (b), the vertical axis represents potential (unit: $\mu V$), and the potential of the electroencephalogram of Ch1 is indicated by a solid line. In (c) and (d), the vertical axis represents frequency power (unit: $\mu V^2$), and transitions in the amount of mixed AC noise are indicated by a dotted line.

A comparison between the states of (a) and (b) in FIG. 20 indicates that, in state (a) where the measurement electrode is left disengaged, the potential reaches 3000 $\mu V$, but thereafter the waveform remains flat. On the other hand, in state (b) where the measurement electrode is once disengaged and then immediately restored, the waveform temporarily becomes flat, but an electroencephalogram waveform appears about several seconds after the electrode restoration. As used herein, "immediately" means about 2 to 3 seconds, for example.

A comparison between the states of (c) and (d) in FIG. 20 indicates that: in state (c) where the ground is left disengaged, the amount of mixed AC noise continues to take values above 10000 $\mu V^2$; however, in state (d) where the ground is once disengaged and then immediately restored, the amount of mixed AC noise temporarily increases to 5000 $\mu V^2$ after the ground is disengaged, but the amount of mixed AC noise after restoration of the ground again returns to low values similar to those before the ground is disengaged.

The comparisons between (a) and (b) and between (c) and (d) have led to a finding concerning the measurement electrode that an electroencephalogram waveform appears immediately after electrode restoration following the insufficiency detection. Therefore, by detecting whether an electroencephalogram waveform appears (i.e., the average and/or variance of the electroencephalogram data becomes non-zero) or not after detection of an electrode insufficiency, it is possible to determine whether the measurement electrode has been restored or not. As for the reference electrode, too, it should be possible to determine whether the reference electrode has been restored or not by subjecting an electroencephalogram of the arbitrary electroencephalogram channel to a determination on a similar basis.

The above comparisons have also led to a finding concerning the ground that the amount of mixed AC noise increases in value after an insufficient grounding, but a restoration allows the amount of mixed AC noise to return to the value in the normal state. Therefore, after an insufficient grounding is detected, it is possible to determine whether the ground has been restored or not by detecting whether the once-increased amount of mixed AC noise has returned to its normal value.

Hereinafter, with reference to the drawings, an electrode restoration determination section 21 which is constructed based on this concept will be described.

FIG. 21 shows the functional block construction of a simplified electroencephalogram measurement system 30 according to the present embodiment. Those blocks which have identical counterparts in Embodiment 1 shown in FIG. 9 will be denoted by like reference numerals, and the descriptions thereof will be omitted. In the simplified electroencephalogram measurement system 30, instead of the electrode state determination processing section 19 shown in FIG. 9, an electrode state determination processing section 19a is provided. As compared to the electrode state determination processing section 19, the electrode restoration determination section 21 for determining electrode restoration is added to the electrode state determination processing section 19a. The electrode restoration determination section 21 determines whether an electrode which became insufficient has been restored to a state which again enables electroencephalogram measurement. For example, the electrode restoration determination section 21 is introduced by newly providing similar hardware to that of the insufficient electrode determination section 14 shown in FIG. 11, and is connected via the bus 100. Alternatively, the program 144 shown in FIG. 11 may be adapted so that the CPU 141, RAM 142, and ROM 143 function as the insufficient electrode determination section 14 at one point in time, and as the electrode restoration determination section 21 at another point in time. The latter example is realized by the program 154 containing not only the procedure of processing by the insufficient electrode determination section 14 but also the procedure of processing by the electrode restoration determination section 21, which is described below. Note that the information of an electrode state that has been determined through the processing by the insufficient electrode determination section 14 is passed onto the processing by the electrode restoration determination section 21, whereby the below-described processes are executed.

FIG. 22 is a flowchart showing a procedure of processing by the simplified electroencephalogram measurement system 30, to which the processing by the electrode restoration determination section 21 is added. As the additional processing by the electrode restoration determination section 21, after the process of notifying electrode insufficiencies (step S1106), a process of determining whether a proper state of attachment has been restored from an insufficient wearing state (step S2000) is added.

The details of the electrode restoration determination process (step S2000 in FIG. 22) performed by the electrode restoration determination section 21 are shown in FIG. 23. Hereinafter, with reference to FIG. 23, the details of the electrode restoration determination process performed by the electrode restoration determination section 21 will be described.

In FIG. 21, when an electrode insufficiency is detected by the insufficient electrode determination section (step S1106 in FIG. 22), the flowchart of FIG. 23 is executed. At step S2101, the electrode restoration determination section 21 begins electroencephalogram measurement for determination of electrode restoration. The electroencephalogram measurement is performed by the electroencephalogram measurement section 11.

At step S2102, based on the type of the insufficient electrode determination section 14, the electrode restoration determination section 21 changes the process of restoration. In the case where the insufficient electrode is the reference electrode 22 or the measurement electrodes 23, a determination of electrode restoration is made based on steps S2103 and S2104. On the other hand, in the case where the insufficient electrode is the ground 21, a restoration determination is made through the processes of steps S2105 and S2106.

First, the restoration determination process for the reference electrode 22 and the measurement electrodes 23 will be described.

At step S2103, from the measured electroencephalogram, the electrode restoration determination section 21 extracts an electroencephalogram channel that includes the insufficient electrode. For example, Ch1 is extracted in the case of the measurement electrode 23b. In the case of the reference electrode, either Ch1 or Ch2 is extracted, since it is included in both Ch1 and Ch2. The electrode restoration determination section 21 calculates an average value and variance of the electroencephalogram signal during a certain period (e.g., 1 second). Note that, unless the state of electrode attachment has been restored, the signal to be processed herein does not qualify as an "electroencephalogram signal", strictly speaking; however, it will nonetheless be referred to as an "electroencephalogram signal" for convenience.

At step S2104, the electrode restoration determination section 21 determines whether the average value and variance calculated at step S2103 are both 0 or not. This is equivalent to determining whether the measured electroencephalogram is flat or not. If both of the average value and variance are 0, the electroencephalogram is flat, i.e., no electroencephalogram is being detected from that electrode, which means that the insufficiency(s) has not been eliminated yet.

Thus, when the electroencephalogram is flat, it can be said that the insufficient electrodes have not been eliminated, and therefore the electrode restoration determination section 21 returns the process to step S2101 to continue determination of electrode restoration until the insufficiencies are eliminated. When the electroencephalogram is no longer flat and an electroencephalogram begins to be measured, it can be said that the electrode insufficiencies have been eliminated, and therefore the electrode restoration determination section 21 notifies the insufficiency cause estimation section 15 that the insufficiencies the measurement electrodes 23 and the reference electrode 22 have been eliminated. Thereafter, the process is ended.

Upon receiving the notification from the electrode restoration determination section 21, the insufficiency cause estimation section 15 again performs an insufficiency cause estimation.

Next, the restoration determination process for the ground 21 will be described.

FIG. 23 is referred to again. At step S2105, with respect to each channel of the measured electroencephalogram, the electrode restoration determination section 21 extracts an electroencephalogram over a certain period (e.g., 1 second) and calculates an amount of mixed AC noise.

At step S2106, the electrode restoration determination section 21 determines whether the calculated amounts of mixed AC noise in all channels exceed a threshold value or not. For example, the threshold value is set to 1700 $\mu V^2$, which was utilized by the insufficient electrode determination section 14 for determining an insufficiency of the ground 21. If the amounts of mixed AC noise in all channels exceed this threshold value, the electrode restoration determination section 21 determines that the insufficiency of the ground 21 has not been eliminated, and returns the process to step S2101. Thus, determination of electrode restoration is continued until the insufficient grounding is eliminated. If the increase in the amounts of mixed AC noise subsides so that the amounts become below the threshold value, the electrode restoration determination section 21 determines that the insufficiency of the ground 21 has been eliminated. Then, the insufficiency of the ground 21 instructs the output section 12 to notify the user 10 that the insufficiency of the ground 21 has been eliminated, and the processing by the electrode restoration determination section 21 is ended. The notice of restoration of the ground via the output section 12 is made in a similar manner to the notice of restoration of the measurement electrode 23 or the reference electrode 22 at step S2107.

By detecting a characteristic feature matching each insufficient electrode, which appears when the insufficient electrode is restored, as in step S2104 or S2106 above, it becomes possible to perform an electrode restoration determination process.

Thus, due to the addition of the electrode restoration determination section 21, after an electrode insufficiency occurs, insufficiency determination is not performed until the insufficient electrode is restored. This makes it unnecessary for the user to perform excessive corrections of the state of electrode attachment, whereby the burden of the user in wearing a housing having electrodes incorporated therein for stable electroencephalogram measurement is reduced.

(Embodiment 3)

By using the simplified electroencephalogram measurement system of Embodiment 1, the user 10 is able to immediately confirm whether the state of electrode attachment is sufficient or not when wearing a housing having electrodes incorporated therein for electroencephalogram measurement. Moreover, when there is any insufficiency in electrode attachment, it is possible to know whether the insufficiency cause is disagreement of the housing shape or hair pinching. This eliminates the possibility of mistakenly adopting a remedy which is really meant for a different cause, e.g., adopting a remedy for hair pinching even though what is actually occurring is disagreement between the head shape and the housing shape. Thus, stable electroencephalogram measurement can be realized with ease.

However, when disagreement occurs between the head shape and the housing shape, the user is unable to know which housing else should be worn next; that is, the user needs to try on a number of housings. This is troublesome to the user.

Therefore, in the present embodiment, the characteristics of a plurality of housing shapes are retained, and an optimum housing is recommended at times of shape disagreement. Thus, the number of trials and errors in housing-wearing by the user is reduced, thus alleviating the user's trouble.

FIG. 24 shows the functional block construction of a simplified electroencephalogram measurement system 40 according to the present embodiment. The simplified electroencephalogram measurement system 40 includes an electroencephalogram measurement/processing section 18 and an electrode state determination processing section 19b. Those blocks which have identical counterparts in FIG. 9 will be denoted by like reference numerals, and the descriptions thereof will be omitted. The simplified electroencephalogram measurement system 40 has a hardware construction as shown in FIG. 11. The simplified electroencephalogram measurement system 40 shown in FIG. 24 is implemented by executing a program that defines a process which is different from the program 154 in the insufficiency cause estimation section 15 described in Embodiment 1.

One large difference of the simplified electroencephalogram measurement system 40 of the present embodiment from the simplified electroencephalogram measurement system 20 of Embodiment 1 is that an optimum housing recommendation section 32 is additionally provided. Also, an insufficiency cause estimation section 31 is provided in the place of the insufficiency cause estimation section 15, thus altering the process for each insufficiency cause.

Hereinafter, the insufficiency cause estimation section 31 and the optimum housing recommendation section 32 will be described.

Similarly to the insufficiency cause estimation section 15, the insufficiency cause estimation section 31 estimates an insufficiency cause based on the number and spatial pattern of insufficient electrodes determined by the insufficient electrode determination section 14. The information concerning insufficient electrode positions is acquired by referring to the electrode position storing section 16. The insufficiency cause estimation section 31 of the present embodiment differs from the insufficiency cause estimation section 15 in that, when the insufficiency cause is disagreement between the head shape and the housing shape, this information is notified to the optimum housing recommendation section 32.

The optimum housing recommendation section 32 retains the characteristics of a plurality of housing shapes, and based on the information of shape disagreement received from the insufficiency cause estimation section 31 and on the shape of the housing currently worn by the user, identifies an optimum housing to be next worn by the user.

Next, with reference to the flowchart of FIG. 25, a procedure of processing by the insufficiency cause estimation section 31 and the optimum housing recommendation section 32 will be described. In FIG. 25, any step at which the same process as that of the simplified electroencephalogram measurement system 20 (FIG. 17) is executed is denoted by a like reference numeral, and the description thereof is omitted.

At step S3101, the insufficiency cause estimation section 31 estimates the insufficiency cause to be disagreement between the head shape and the housing shape, and notifies the information of the spatial pattern of insufficient electrodes to the optimum housing recommendation section 32.

At step S3102, based on the spatial pattern of insufficient electrodes received from the insufficiency cause estimation section 31 and the shape of the housing currently worn by the user, and also on the characteristic features of the plurality of housing shapes retained in the optimum housing recommendation section 32, the optimum housing recommendation section 32 identifies an optimum housing to be next worn by the user. FIG. 26 shows exemplary characteristics of the plurality of housing shapes retained in the optimum housing recommendation section 32. In FIG. 26 for example, for each housing, information such as size, general shape (SHAPE 1), and detailed shape (SHAPE 2) is retained as the characteristics of the housing shape.

Assume for example that the current housing shape as received from the insufficiency cause estimation section is "housing A" in FIG. 26 and the spatial pattern of insufficient electrodes is identical to that of "dent in the central portion" as shown in FIG. 18. In this case, with respect to housing A being currently worn by the user, the optimum housing recommendation section 32 determines that housing B, which is more dented in the central portion than is housing A, is optimum, without changing the size and the general shape (SHAPE 1). Then, the optimum housing recommendation section 32 outputs the information concerning this housing to be worn to the user, via the output section 12. FIG. 27 shows an example of information to be presented to the user concerning the housing to be next worn by the user.

Through such processes, when the insufficiency cause is disagreement between the head shape and the housing shape, a new, optimum housing can be recommended.

With the simplified electroencephalogram measurement system 40 of the present embodiment, when the insufficiency cause of electrode attachment is disagreement between the head shape and the housing shape, a housing to be next worn by the user can be identified and recommended. Thus, the number of trials and errors in housing-wearing by the user is reduced, and identification of an optimum housing which is suitable to the head shape is facilitated, thus significantly reducing the trouble of searching for a housing shape that will enable stable electroencephalogram measurement.

A simplified electroencephalogram measurement system according to the present disclosure is broadly applicable to an electroencephalogram interface system which determines the state or intent of a user from a measured electroencephalogram signal, and feeds back a result of determination. Specifically, in the case where electroencephalogram measurements are taken in a daily-life environment by using dry electrodes, it will be useful to incorporate the simplified electroencephalogram measurement system according to the present disclosure into a wearable device such as an electroencephalograph, an HMD, or a headset, in order to determine whether the state of attachment of the dry electrodes has become insufficient or not. The simplified electroencephalogram measurement system according to the present disclosure is useful for constructing such an electroencephalogram interface system for inferring the state or intent of a user, and may be implemented as a computer program for incorporation therein.

While the present disclosure has been described with respect to the exemplary embodiments thereof, it will be apparent to those skilled in the art that the disclosed examples may be modified in numerous ways and may assume many embodiments other than those specifically described above. Accordingly, it is intended by the appended claims to cover all modifications that fall within the true spirit and scope of the disclosure.

What is claimed is:

1. An electroencephalogram measurement system comprising:
    an electroencephalogram measurement unit having a plurality of electrodes being disposed in one housing, the plurality of electrodes including a reference electrode, measurement electrodes and a ground, for measuring an electroencephalogram signal between the reference electrode and a measurement electrode on the basis of the ground, the plurality of electrodes constituting a plurality of electroencephalogram measurement channels, such that each electroencephalogram measurement channel is defined by at least the reference electrode and a measurement electrode;
    an electrode position storing unit for storing positions at which the plurality of electrodes respectively come in contact with a user when the user wears the electroencephalogram measurement unit;
    a frequency analysis unit for analyzing a frequency power of the electroencephalogram signal measured by the electroencephalogram measurement unit with respect to each electroencephalogram measurement channel;
    an insufficient electrode determination unit for distinguishing whether a state of attachment of each electrode is sufficient or not by comparing the frequency power analyzed by the frequency analysis unit against a predetermined first threshold value; and
    an insufficiency cause estimation unit for: determining the number of insufficient electrodes distinguished as insufficiently worn at the insufficient electrode determination unit; determining a position at which each insufficient electrode determined as insufficiently worn at the insufficient electrode determination unit is in contact with the user, by referring to the positions of the plurality of electrodes stored in the electrode position storing unit; and estimating a cause for the insufficient state of attachment of the insufficient electrode or electrodes that corresponds to the determined number of insufficient electrodes and position of each insufficient electrode, by comparing the determined number of insufficient electrodes and position of each insufficient electrode to insufficiency pattern data defining associations between a number of insufficient electrodes, a position at which each insufficient electrode comes in contact with the user, and causes for the insufficient state of attachment of an insufficient electrode or electrodes.

2. The electroencephalogram measurement system of claim 1, wherein the insufficiency pattern data defines the associations so that, when the number of insufficient electrodes is greater than a second threshold value and there are contiguous insufficient electrodes adjoining one another, the cause for the insufficient state of attachment of the insufficient electrode or electrodes is associated with disagreement between a head shape of the user and shape of the housing of the electroencephalogram measurement unit.

3. The electroencephalogram measurement system of claim 1, wherein the insufficient electrode determination unit extracts a noise amount parameter from the result of the frequency power analysis, and if the noise amount parameter has a value exceeding a predetermined third threshold value, determines that the ground is insufficiently worn.

4. The electroencephalogram measurement system of claim 3, wherein the insufficient electrode determination unit further extracts a total frequency power parameter from the result of the frequency power analysis, and if the total frequency power parameter has a value exceeding a predetermined second threshold value, determines that the reference electrode or a measurement electrode is insufficiently worn.

5. The electroencephalogram measurement system of claim 1, wherein,
    the electroencephalogram measurement unit uses a plurality of sets of electrodes each including a ground, a reference electrode, and a measurement electrode, to measure an electroencephalogram signal with each set;
    the frequency analysis unit performs a frequency power analysis of each electroencephalogram signal; and
    the insufficient electrode determination unit
    extracts a noise amount parameter from a result of the frequency power analysis of each electroencephalogram signal, and if all of the noise amount parameters have values exceeding a predetermined third threshold value, determines that the ground is insufficiently worn, and
    extracts a total frequency power parameter from the result of the frequency power analysis of each electroencephalogram signal, and if all of the total frequency power parameters have values exceeding a predetermined fourth threshold value, determines that the reference electrode is insufficiently worn, or if some of the extracted total frequency power parameters have values exceeding the fourth threshold value, determines that a measurement electrode is insufficiently worn.

6. The electroencephalogram measurement system of claim 1, wherein the electroencephalogram measurement unit measures a first potential difference and a second potential difference, the first potential difference being a potential difference between the ground and the reference electrode and the second potential difference being a potential difference between the ground and the measurement electrode, and measures the electroencephalogram signal based on a difference between the second potential difference and the first potential difference.

7. The electroencephalogram measurement system of claim 1, wherein,
a noise being steadily mixed from an external environment at a previously identified frequency is superposed on the electroencephalogram signal; and
from the result of the frequency analysis, the insufficient electrode determination unit extracts a frequency power of the noise as a noise amount parameter.

8. The electroencephalogram measurement system of claim 7, wherein the previously identified frequency is a frequency of a commercial-power noise of a device which is in the external environment.

9. The electroencephalogram measurement system of claim 7, further comprising an electrode restoration determination unit for determining, based on a signal measured by using an insufficient electrode which is determined as insufficiently worn, whether the insufficiency in the state of attachment of the insufficient electrode has been eliminated or not, wherein,
when the insufficient electrode determined as insufficiently worn is the ground,
the electrode restoration determination unit extracts the noise amount parameter from the result of the frequency power analysis of the signal as measured by using the insufficient electrode, and, if the noise amount parameter has a value exceeding a predetermined third threshold value, the electrode restoration determination unit determines that the insufficiency in the state of attachment of the insufficient electrode has not been eliminated, or if the noise amount parameter does not have a value exceeding a predetermined third threshold value, the electrode restoration determination unit determines that the insufficiency in the state of attachment of the insufficient electrode has been eliminated.

10. The electroencephalogram measurement system of claim 1, further comprising an output unit for outputting a result of estimation by the insufficient electrode estimation unit, wherein,
if no insufficient electrode is detected by the insufficient electrode determination unit, the output unit outputs an indication of a sufficient state of attachment.

11. The electroencephalogram measurement system of claim 1, further comprising an output unit for outputting a result of estimation by the insufficient electrode estimation unit, wherein,
if any insufficient electrode is detected by the insufficient electrode determination unit, the output unit outputs an indication of a position of the insufficient electrode.

12. The electroencephalogram measurement system of claim 1, wherein, when the number of insufficient electrodes distinguished as insufficiently worn at the insufficient electrode determination unit is greater than a predetermined second threshold value, the insufficiency cause estimation unit estimates the cause for the insufficient state of attachment of the insufficient electrode or electrodes to be disagreement between a head shape of the user and shape of the housing of the electroencephalogram measurement unit if a correlation coefficient between a position or positions of the insufficient electrode or electrodes determined as insufficiently worn and a position or positions of an insufficient electrode or electrodes in the insufficiency pattern data exceeds a predetermined threshold value.

13. The electroencephalogram measurement system of claim 12, further comprising an optimum housing recommendation unit for, when cause for the insufficient state of attachment is estimated by the insufficiency cause estimation unit to be disagreement between the head shape and the shape of the housing, recommending an optimum housing based on information of disagreement in head shape and the shape of the current housing.

14. An electroencephalogram measurement system comprising:
an electroencephalogram measurement unit having a plurality of electrodes being disposed in one housing, the plurality of electrodes including a reference electrode and measurement electrodes, for measuring an electroencephalogram signal of a user between the reference electrode and a measurement electrode, the plurality of electrodes constituting a plurality of electroencephalogram measurement channels, such that each electroencephalogram measurement channel is defined by at least the reference electrode and a measurement electrode;
a frequency analysis unit for analyzing a frequency power of the electroencephalogram signal measured by the electroencephalogram measurement unit with respect to each electroencephalogram measurement channel;
an insufficient electrode determination unit for distinguishing whether a state of attachment of each electrode is sufficient or not by comparing the frequency power analyzed by the frequency analysis unit against a predetermined first threshold value; and
an insufficiency cause estimation unit for estimating a cause for the insufficient state of attachment of the insufficient electrode or electrodes, wherein, when the number of insufficient electrodes distinguished as insufficiently worn at the insufficient electrode determination unit is equal to or less than a predetermined second threshold value, the insufficiency cause estimation unit estimates the cause to be existence of hair of the user between a head of the user and the insufficient electrode or electrodes distinguished as insufficiently worn.

15. An electroencephalogram measurement system comprising:
a frequency analysis unit for analyzing a frequency power of an electroencephalogram signal measured by an electroencephalogram measurement section having a plurality of electrodes being disposed in one housing, the plurality of electrodes including a reference electrode, measurement electrodes and a ground, the electroencephalogram measurement section measuring an electroencephalogram signal between the reference electrode and a measurement electrode on the basis of the ground, the plurality of electrodes constituting a plurality of electroencephalogram measurement channels such that each electroencephalogram measurement channel is defined by at least the reference electrode and a measurement electrode, the frequency power of the electroencephalogram signal being analyzed with respect to each electroencephalogram measurement channel;
an insufficient electrode determination unit for distinguishing whether a state of attachment of each electrode is sufficient or not by comparing the frequency power analyzed by the frequency analysis unit against a predetermined first threshold value; and an insufficiency cause estimation unit for determining the number of insufficient electrodes distinguished as insufficiently worn at the insufficient electrode determination unit and a position at which each insufficient electrode is in contact with the user, and estimating a cause for the insufficient state of attachment of the insufficient electrode or electrodes that corresponds to the determined number and positions of insufficient electrodes, by comparing the determined number of insufficient electrodes and position of each insufficient electrode to insufficiency pattern data defining associations between a number of insufficient electrodes, a position at which each insufficient electrode comes in contact with the user, and causes for the insufficient state of attachment, wherein the insufficiency cause estimation unit determines the position at which each insufficient electrode is in contact with the user by referring to positions of the plurality of electrodes stored in an electrode position storing unit for storing positions at which the plurality of electrodes respectively come in contact with a user when the user wears the electroencephalogram measurement unit.

16. An electroencephalogram measurement method comprising:

an electroencephalogram measurement step of measuring an electroencephalogram signal of a user with an electroencephalogram measurement unit by using a plurality of electrodes disposed in one housing, the plurality of electrodes including a reference electrode, measurement electrodes and a ground, the electroencephalogram signal being measured between the reference electrode and a measurement electrode on the basis of the ground, the plurality of electrodes constituting a plurality of electroencephalogram measurement channels, such that each electroencephalogram measurement channel is defined by at least the reference electrode and a measurement electrode;

a frequency analysis step of analyzing with a frequency analysis unit a frequency power of the electroencephalogram signal measured in the electroencephalogram measurement step with respect to each electroencephalogram measurement channel;

an insufficient electrode determination step of, with an insufficient electrode determination unit, distinguishing whether a state of attachment of each electrode is sufficient or not by comparing the frequency power analyzed in the frequency analysis step against a predetermined first threshold value;

a determination step of, with an insufficiency cause estimation unit, determining the number of insufficient electrodes distinguished as insufficiently worn at the insufficient electrode determination step, and determining a position at which each insufficient electrode determined as insufficiently worn at the insufficient electrode determination step is in contact with the user by referring to information of positions at which the plurality of electrodes respectively come in contact with the user when the user wears the housing at the electroencephalogram measurement step; and an insufficiency cause estimation step of, with the insufficiency cause estimation unit, estimating a cause for the insufficient state of attachment of the insufficient electrode or electrodes that corresponds to the determined number of insufficient electrodes and position of each insufficient electrode, by comparing the determined number of insufficient electrodes and position of each insufficient electrode to insufficiency pattern data defining associations between a number of insufficient electrodes, a position at which each insufficient electrode comes in contact with the user, and causes for the insufficient state of attachment.

17. A non-transitory computer-readable storage medium storing a computer program, to be executed by a computer for electroencephalogram measurement, wherein the computer program causes the computer to execute the steps of:

an electroencephalogram measurement step of measuring an electroencephalogram signal of a user by using a plurality of electrodes disposed in one housing, the plurality of electrodes including a reference electrode, measurement electrodes and a ground, the electroencephalogram signal being measured between the reference electrode and a measurement electrode on the basis of the ground, the plurality of electrodes constituting a plurality of electroencephalogram measurement channels, such that each electroencephalogram measurement channel is defined by at least the reference electrode and a measurement electrode;

a frequency analysis step of analyzing a frequency power of the electroencephalogram signal measured in the electroencephalogram measurement step with respect to each electroencephalogram measurement channel;

an insufficient electrode determination step of distinguishing whether a state of attachment of each electrode is sufficient or not by comparing the frequency power analyzed in the frequency analysis step against a predetermined first threshold value;

a determination step of determining the number of insufficient electrodes distinguished as insufficiently worn at the insufficient electrode determination step, and determining a position at which each insufficient electrode determined as insufficiently worn at the insufficient electrode determination step is in contact with the user by referring to information of positions at which the plurality of electrodes respectively come in contact with the user when the user wears the housing at the electroencephalogram measurement step; and an insufficiency cause estimation step of estimating a cause for the insufficient state of attachment of the insufficient electrode or electrodes that corresponds to the determined number of insufficient electrodes and position of each insufficient electrode, by comparing the determined number of insufficient electrodes and position of each insufficient electrode to insufficiency pattern data defining associations between a number of insufficient electrodes, a position at which each insufficient electrode comes in contact with the user, and causes for the insufficient state of attachment.

\* \* \* \* \*